(12) United States Patent
Bheemireddy et al.

(10) Patent No.: US 12,322,757 B2
(45) Date of Patent: *Jun. 3, 2025

(54) ISATIN DERIVATIVE REDOXAMER FOR ELECTROCHEMICAL DEVICE

(71) Applicant: UCHICAGO ARGONNE, LLC, Chicago, IL (US)

(72) Inventors: Sambasiva Reddy Bheemireddy, Woodridge, IL (US); Lu Zhang, Naperville, IL (US); Zhengcheng Zhang, Naperville, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 155 days.

This patent is subject to a terminal disclaimer.

(21) Appl. No.: 18/209,397

(22) Filed: Jun. 13, 2023

(65) Prior Publication Data

US 2023/0327205 A1      Oct. 12, 2023

Related U.S. Application Data

(63) Continuation of application No. 17/191,872, filed on Mar. 4, 2021, now Pat. No. 11,715,844.

(51) Int. Cl.
*H01M 10/0567* (2010.01)
*C07D 209/38* (2006.01)
*H01M 8/18* (2006.01)
*H01M 10/0525* (2010.01)

(52) U.S. Cl.
CPC ...... *H01M 10/0567* (2013.01); *C07D 209/38* (2013.01); *H01M 8/188* (2013.01); *H01M 10/0525* (2013.01); H01M 2300/0025 (2013.01)

(58) Field of Classification Search
CPC .............. H01M 10/0567; H01M 8/188; C07D 209/38
USPC .................................................. 429/108, 188
See application file for complete search history.

(56) References Cited

U.S. PATENT DOCUMENTS

| | | |
|---|---|---|
| 9,905,876 B2 | 2/2018 | Schubert et al. |
| 11,715,844 B2 * | 8/2023 | Bheemireddy ..... H01M 10/052 429/108 |
| 2014/0370403 A1 | 12/2014 | Narayan et al. |
| 2015/0050561 A1 | 2/2015 | Zhang et al. |
| 2020/0052302 A1 | 2/2020 | Mallet et al. |

FOREIGN PATENT DOCUMENTS

| | | | |
|---|---|---|---|
| CN | 109880138 A * | 6/2019 | |
| CN | 110903449 A * | 3/2020 | ............. C08G 10/00 |
| JP | 2006-286500 | 10/2006 | |

OTHER PUBLICATIONS

Duan, W., et al., "A symmetric organic-based nonaqueous redox flow battery and its state of charge diagnostics by FTIR",J. Mater. Chem. A4, pp. 5448-5456 (2016).

(Continued)

*Primary Examiner* — Sean P Cullen
(74) *Attorney, Agent, or Firm* — Foley & Lardner LLP

(57) ABSTRACT

An electrochemical device includes a compound that is an isatin derivative. The electrochemical device may be a lithium ion battery, a sodium ion battery, or a redox flow battery, and the isatin derivative may be a bipolar redox active material.

17 Claims, 4 Drawing Sheets

(56) References Cited

OTHER PUBLICATIONS

Lee, et al., Redox-Active Organic Compounds for Future Sustainable Energy Storage System, 2020, Advanced Energy Materials, 10, 2001445 (2020).
Sun, et al., "High Throughput Screening of Organic Electrode Materials for Lithium Battery by Theoretical Method", 2015, The Journal of Physical Chemistry C, 119, 25770-25777 (2015).
Wang, Q., et al., "Regioselective/electro-oxidative intermolecular [3 2] annulation for the preparation of indolines," Chem. Sci. 11, pp. 2181-2186 (2020).
Yen, et al., Dialkyl Phosphite-Initiated Cyclopropanation of a B-Unsaturated Ketones Using a-Ketoesters or Isatin Derivatives, 2017, The Journal of Organic Chemistry, 82, 3252-3261 (2017).

* cited by examiner

ISATIN DERIVATIVE REDOXAMER FOR ELECTROCHEMICAL DEVICE

GOVERNMENT RIGHTS

This invention was made with government support under Contract No. DE-AC02-06CH11357 awarded by the United States Department of Energy to UChicago Argonne, LLC, operator of Argonne National Laboratory. The government has certain rights in the invention.

CROSS REFERENCE TO RELATED APPLICATIONS

This application claims the benefit of priority to U.S. patent application Ser. No. 17/191,872 filed Mar. 4, 2021, which is hereby incorporated by reference, in its entirety for any and all purposes.

FIELD

The present technology is generally related to electrochemical devices that incorporate a bipolar redox active material. More specifically, it is related to electrochemical devices that incorporate an isatin derivative as a catholyte and/or anolyte material in a redox flow battery, or as a redox shuttle material in a conventional lithium ion battery or sodium ion battery.

BACKGROUND

Renewable energy sources such as solar and wind powers are making significant inroads into the global energy supply as environment-friendly alternatives to fossil fuels. Like all methods of power generation, these renewable energy sources are not perfect. Despite technical bottlenecks hampering their overall performance, the intermittent nature of these energy sources, meaning that energy can only be produced when the sun is shining or the wind is blowing, severely restricts their real-world applicability because the grid itself has very limited energy storage capability. As a solution to this dearth of storage capability, grid-scale energy storage technologies have raised enormous amounts of interest from both industry and academia, with redox flow batteries (RFDs) among the leaders in performance. Due to attractive features such as facile scale-tip of energy capacity, long-period steady discharge at peak power, and intrinsic high safety, modem redox flow batteries have held significant potential since their debut in the 1970s.

When RFBs serve as power sources to external circuits, two solutions with electro-activated materials readily dissolved are being pumped into a cell chamber that is divided into two compartments by separators that only allow supporting electrolytes to migrate for charge balancing. The pioneer of modern RFBs was an iron-chromium aqueous system developed by NASA and the aqueous systems by far are the mainstay of the RB technologies. However, drawbacks such as low voltage window (<1.5 V) and limited choice of active materials present major technical challenges yet to be addressed.

Non-aqueous RFB systems demonstrate a vast number of advantages over their aqueous counterparts, implying the potential of meeting stringent requirements for ideal RFBs. Non-aqueous RFBs have wider voltage window (>2 V) than their aqueous counterparts, and with a large variety of organic solvents and an expanding list of acceptable redox active materials, they are tunable to particular applications. In order to improve the performance of non-aqueous RFBs at minimal architectural and monetary cost, tremendous research efforts have been focused on the development of novel active materials with desired properties. Recently, lowering the molecular weights of active species has drawn significant amount of attentions in order to increase the energy density of non-aqueous RFBs. Although organic molecules present possibilities of facile tailoring of chemical structures, challenges lie in balancing the molecule weight and the electrochemical stability. For example, 2,5-di-tert-butyl-1,4-bis(2-methoxyethoxy)benzene (DBBB), one of the most successful classes of stable catholyte for non-aqueous RBs, requires two bulky tertbutyl groups, which constitute over one third of the mass of the entire molecule, to provide efficient steric shielding to suppress the decomposition of the molecule in electrochemical environments. Developing low molecular weight active materials from readily available or sustainable starting materials greatly helps to improve energy density and reduce the cost of the RFBs.

SUMMARY

In one aspect, an electrochemical device includes a compound represented by Formula I:

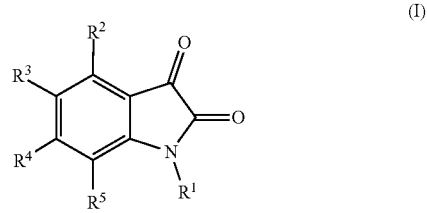

(I)

wherein:

$R^1$, $R^2$, $R^3$, $R^4$, and $R^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of $R^1$, $R^2$, $R^3$, $R^4$, and $R^5$ is a linker to a polymer backbone, where the linker is absent, a carbonyl, a alkyl ester group, aryl-E, E-aryl, alkylene, or -alkyl-O-alkyl-;

E is an alkylene or alkyl-O-alkyl;

at least one of $R^1$, $R^2$, $R^3$, $R^4$, and $R^5$ is other than H;

when $R^1$ is H, $R^3$ is other than methyl.

In such embodiments, the electrochemical device may be a redox flow battery or lithium ion battery.

In another aspect, an electrochemical device is provided including a cathode, an anode, a separator disposed between the cathode and the anode, and an electrolyte that includes a non-aqueous solvent, a salt, and an isatin derivative that is other than isatin and 5-methylisatin, wherein the electrochemical device is a lithium ion battery or a sodium ion battery. The isatin derivative may be used in the electrochemical device such as these as a redox shuttle additive to prevent or mitigate overcharging and/or overdischarging in the device. In any such embodiments, the isatin derivative may be a compound represented by Formula I:

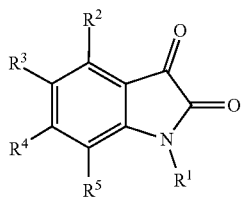

(I)

wherein:
R$^1$, R$^2$, R$^3$, R$^4$, and R$^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of R$^1$, R$^2$, R$^3$, R$^4$, and R$^5$ is a linker to a polymer backbone, where the linker is absent, a carbonyl, aryl-E, E-aryl, a alkyl ester group, alkylene, or -alkyl-O-alkyl-;
E is an alkylene or alkyl-O-alkyl;
at least one of R$^1$, R$^2$, R$^3$, R$^4$, and R$^5$ is other than H;
when R$^1$ is H, R$^3$ is other than methyl.

In another aspect, an electrochemical device is provided that includes a catholyte reservoir containing a catholyte material dissolved in a first non-aqueous solvent, an anolyte reservoir containing an anolyte material dissolved in a second non-aqueous solvent, and a reaction chamber, wherein the first and second non-aqueous solvents are the same or different, the catholyte material, the anolyte material, or both the catholyte material and the anolyte material is an isatin derivative compound, and the electrochemical device is a redox flow battery. In some such embodiments, the isatin derivative compound may be other than isatin and 5-methylisatin. In some such embodiments, the isatin derivative may be a compound represented by Formula I. An advantage of such a redox flow battery is that the catholyte and anolyte may be the same, bipolar active material such that is there is leakage of the catholyte to the anolyte, or vice versa, there is no change in overall chemistry of the device.

In another aspect, a compound is provided as represented by Formula I:

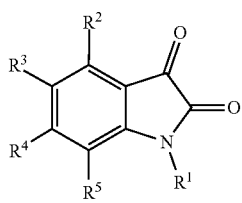

(I)

wherein:
R$^1$, R$^2$, R$^3$, R$^4$, and R$^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of R$^1$, R$^2$, R$^3$, R$^4$, and R$^5$ is a linker to a polymer backbone, where the linker is absent, an alkylenyl, an alkyl-O-alkyl, aryl-E, E-aryl, a carbonyl, or a alkyl ester, wherein E is an alkylene or alkyl-O-alkyl;
at least one of R$^1$, R$^2$, R$^3$, R$^4$, and R$^5$ is other than H;
when R$^1$ is H, R$^3$ is other than methyl; and
where R$^1$ is methyl, R$^3$ and R$^5$ are not both methyl.

DETAILED DESCRIPTION

Figure 1:
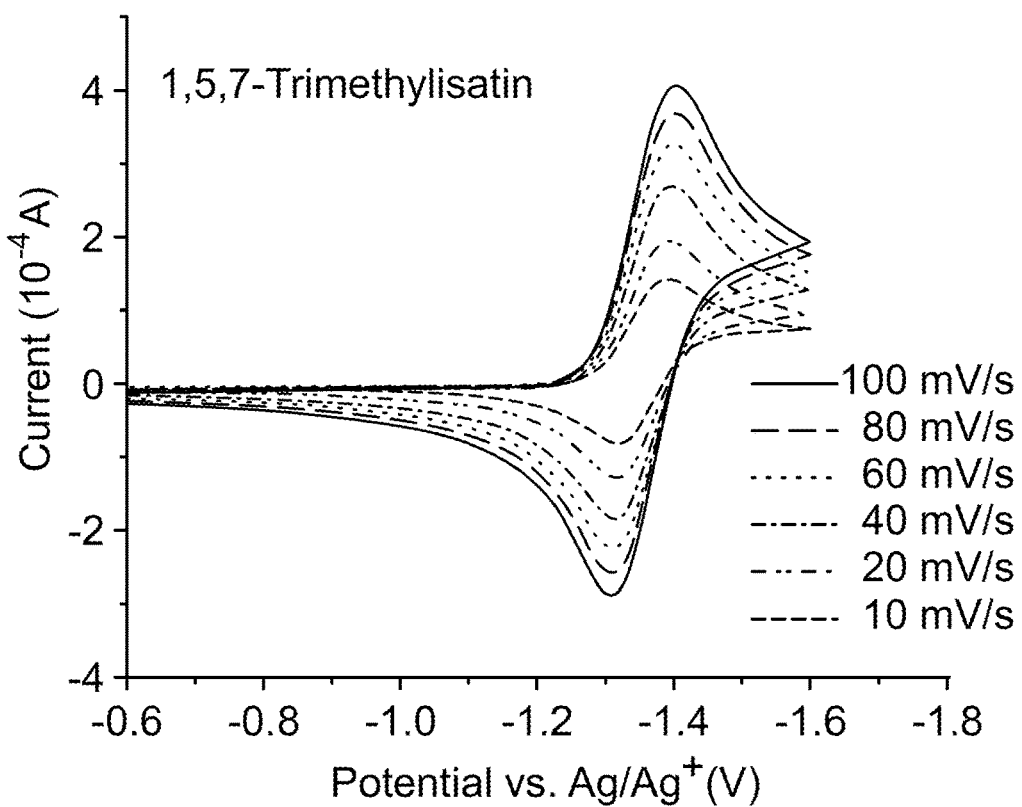
FIG. 1 illustrates cyclic volatammetry scans in the negative direction for an acetonitrile solution of 1,5,7-trimethylisatin (10 mM) with TBAPF$_6$ (0.1 M), at different scan rates, according to Example 3.
Figure 2:
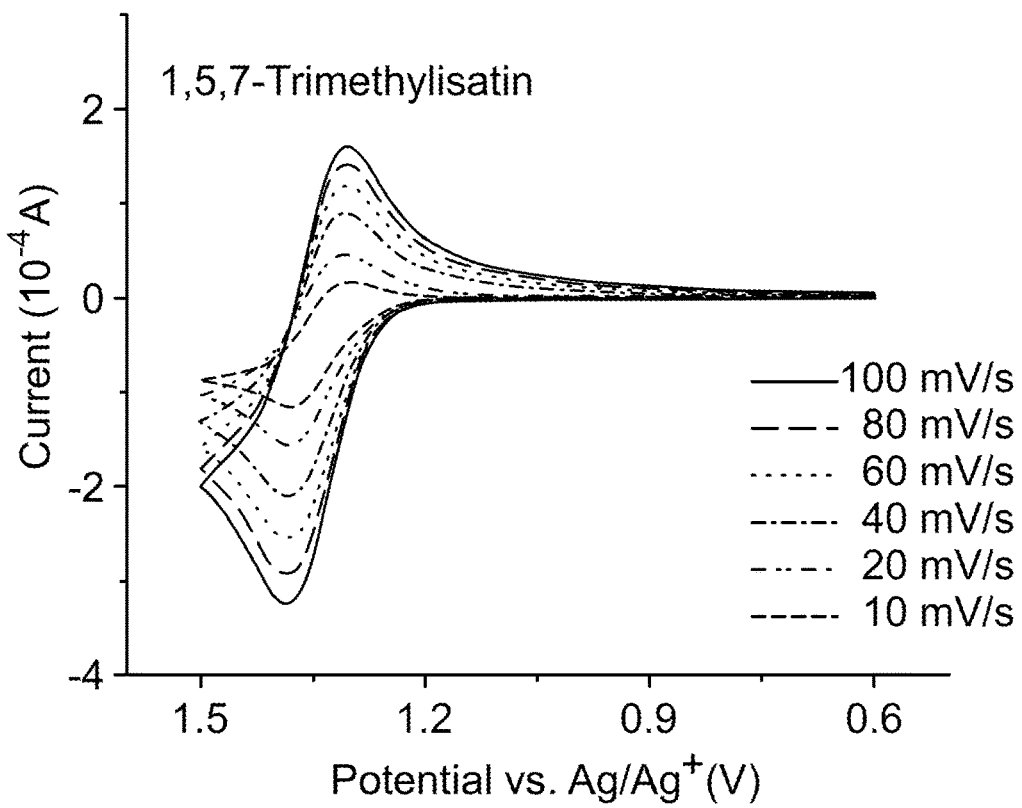
FIG. 2 illustrates cyclic volatammetry scans in the positive direction for an acetonitrile solution of 1,5,7-trimethylisatin (10 mM) with TBAPF$_6$ (0.1 M), at different scan rates, according to Example 3.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term "haloalkyl" is an alkyl group having one or more halo groups. In some embodiments, haloalkyl refers to a per-haloalkyl group. As used herein, "haloalkyl" groups may be unsubstituted (i.e. containing one or more halo groups, but without other substitutions) or substituted (i.e. containing one or more halo groups along with other substitutions as defined above). "Alkoxy" is an —Oalkyl group, where alky is as defined herein.

As used herein, "alkoxy" groups are groups bound through an oxygen to alkyl group and may be represented as a —Oalkyl group.

As used herein, "aryl", or "aromatic," groups are cyclic aromatic hydrocarbons that do not contain heteroatoms. Aryl groups include monocyclic, bicyclic, and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

As used herein, "polyether" refers to a group that is an alkyl group interrupted by an oxygen atom such that one or more ether linkages in the group are present. As used herein, a polyether includes glycols, polyethylene glycol groups, polypropylene glycol groups, etc.

As used herein, "a polymer backbone" refers to the presence of a polymer from which the indicated group may be pendent in one or more of the repeat units. When shown pictorially, the polymer backbone may be represented parenthetically with an "n" indicator, however the "n" is not necessarily a quantity but rather indicates that the repeat unit may be present one or more times in the polymer backbone.

The present inventors have now found that RFBs can be designed based upon a class of isatin-based molecules and oligomers. The isatin-based redoxmers are demonstrated herein to exhibit bipolar redox behavior in non-aqueous solvents, thus can be used a single redox active material for RFB both as positive electrode (or catholyte) and negative electrode (or anolyte) Furthermore, due to their reversible oxidation/reduction reaction at approximately 4.47 V vs. Li/Li+, these molecules may be used as redox shuttles for overcharge protection of high energy density Li-ion or Na-ion batteries. Similarly, these molecules exhibit a reversible reduction/oxidation reaction at approximately 1.8 V vs. Li/Li+, making them good redox shuttle additive candidates for overdischarging protection of high energy density Li-ion or beyond such as Na-ion batteries.

Isatin is a natural product that can be found in plants of the genus *Isatis*, in *Couroupita guianensis*, and in humans as a metabolic derivative of adrenaline. Isatin is represented by the following structure:

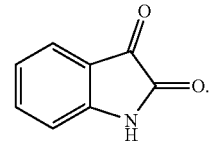 [SMILES: O=C1Nc2ccccc2C1=O]

Derivatization of isatin has been found to result in improved redox character and stability. The isatin derivatives disclosed herein possess bipolar redox behavior, having two redox couples: one at about −1.35 V and another at about +1.34 V (vs. Ag/Ag+) in non-aqueous solvents. The disclosed compounds also exhibit a reversible redox couple at about 4.47 V vs. Li/Li$^+$. The disclosed compounds also exhibit a reversible oxidation/reduction redox couple at about 4.47 V vs. Li/Li$^+$ and a reversible reduction/oxidation couple at 1.88 V vs Li/Li+ The isatin derivatives described herein, including isatin, may be used as bipolar redox materials in redox flow batteries, and some of the isatin derivatives other than isatin itself may be used as redox shuttle additives in Li-ion, Na-ion, K-ion, and multivalent ion battery designed such as for Mg-ion, Ca-ion, and Al-ion.

In one aspect, an electrochemical device is provided, the device including a compound represented by Formula I:

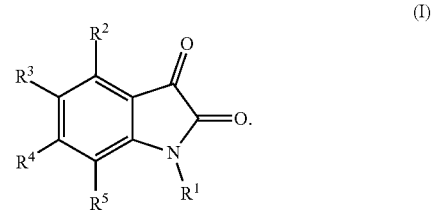

(I)

In Formula I, $R^1$, $R^2$, $R^3$, $R^4$, and $R^5$ may each be independently H, substituted or unsubstituted alkyl, substituted or unsubstituted haloalkyl, substituted or unsubstituted aryl, or substituted or unsubstituted polyether; or any of $R^1$, $R^2$, $R^3$, $R^4$, and $R^5$ may be a linker to a polymer backbone, where the linker is absent, a carbonyl, alkylenyl, -alkyl-O-alkyl-, -aryl-E-, -E-aryl-, or a alkyl ester group, wherein E is alkylenyl or alkyl-O-alkyl. In various embodiments, where the compound is represented by Formula I at least one of $R^1$, $R^2$, $R^3$, $R^4$, and $R^5$ may be other than H, and/or when $R^1$ is H, $R^3$ may be other than methyl.

With regard to Formula I, in some embodiments, $R^1$, $R^2$, $R^3$, $R^4$, and $R^5$ may be each independently H, $C_1$-$C_{10}$ alkyl, $C_1$-$C_{10}$ haloalkyl, or polyether. In some embodiments, $R^1$, $R^2$, $R^3$, $R^4$, and $R^5$ may be each independently H, an alkyl-O-alkyl, methyl, ethyl, n-propyl, i-propyl, n-butyl, sec-butyl, tert-butyl, or polyether. In some embodiments, $R^1$, $R^3$, and $R^5$ may be each independently $C_1$-$C_{10}$ alkyl, and $R^2$ and $R^4$ are H. In some embodiments, $R^1$, $R^3$, and $R^5$ may be each independently methyl, ethyl, n-propyl, i-propyl, n-butyl, sec-butyl, or tert-butyl; and $R^2$ and $R^4$ are H. In some embodiments, $R^1$, $R^3$, and $R^5$ may be each independently methyl or ethyl; and $R^2$ and $R^4$ are H. In some embodiments, $R^1$ is H or alkyl; $R^2$, $R^3$, and $R^4$ are alkoxy such as methoxy or ethoxy, and $R^5$ is H.

In some embodiments of Formula I, $R^3$ may be a substituted aryl group of Formula II:

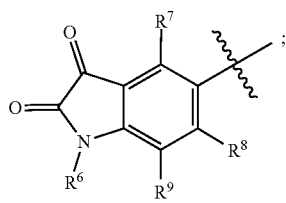

(II)

In Formula II, $R^6$, $R^7$, $R^8$, and $R^9$ may be each independently H, substituted or unsubstituted alkyl, substituted or unsubstituted haloalkyl, or substituted or unsubstituted polyether, or where any of $R^6$, $R^7$, $R^8$, and $R^9$ is a linker to a polymer backbone, where the linker is absent, aryl-E, E-aryl, a carbonyl, alkylenyl, alkyl-O-alkyl, or an alkyl ester group, wherein E is an alkylene or alkyl-O-alkyl. In some embodiments, $R^1$, $R^3$, or $R^6$ may be a linker, L, to a polymer backbone, where the linker is absent, arylalkyl, alkylenyl, -alkyl-O-alkyl-, a carbonyl, or an alkyl ester group.

In some embodiments of Formula I, the compound may be a trimeric structure, where the isatin moiety of Formula I is connected to two other isatin moieties through their $R^3$ positions by a linking group of Formulae:

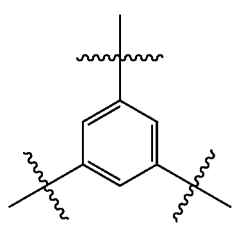

or

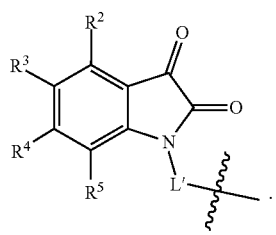

In some embodiments of Formula I, $R^1$ is a group of Formula Ia:

(Ia)

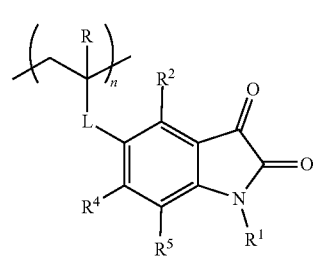

In Formula Ia, $R^2$-$R^5$ are as above, and L' is absent or a linker group. Illustrative L' groups include substituted or unsubstituted alkylenes, alkyl-O-alkyl ether groups, carboxylated groups, and the like.

Where in Formula I, $R^1$ or $R^3$ is a linker, the structure may be represented by Formula III, IIIa, or IV:

(III)

(IV)

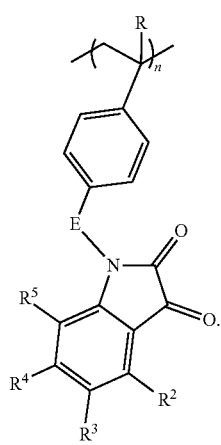

(IIIa)

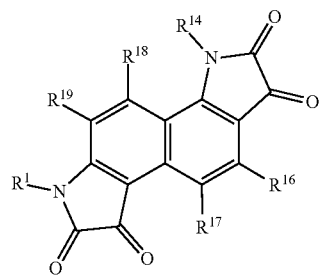

(VII)

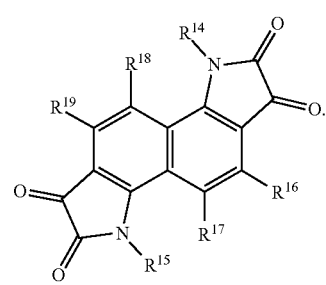

(VIII)

In Formulas III, IIIa and IV, R may be H or alkyl, and n indicates that the group is part of a repeat unit in a polymer backbone. In some embodiments, L may be absent, alkylene, aryl-E, E-aryl, —C(O)—, -alkyl-O-alkyl, or —CH$_2$CH$_2$OC(O)—, wherein E is alkylenyl or alkyl-O-alkyl. In some embodiments where the compound includes Formula III or IIIa, L may be —CH$_2$—, —C(O)— or —CH$_2$CH$_2$OC(O)—. In some such embodiments, R may be CH$_3$. In some embodiments where the compound includes Formula IV, L may be absent. In such embodiments, R may be H.

The multimers, or polymers, described herein (including those of Formulas III, IIIa, and IV) may be used in the catholyte, anolyte, or both the catholyte and anolyte of a redox flow battery. They are believed to improve the energy density of the anolyte and/or catholyte and minimize or prevent cross-over through the membrane.

In a second aspect, an electrochemical device is provided, where the device includes a compound represented by Formula V, VI, VII, or VIII:

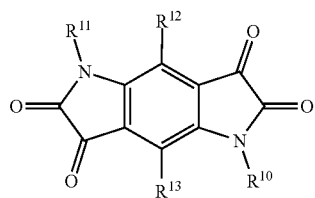

(V)

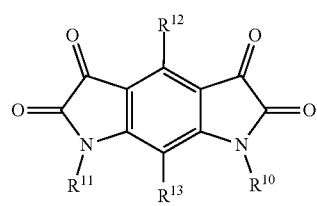

(VI)

In Formulas V, VI, VII, and VIII, $R^{10}$, $R^{11}$, $R^{12}$, $R^{13}$, $R^{14}$, $R^{15}$, $R^{16}$, $R^{17}$, $R^{18}$, and $R^{19}$ may be each independently H, substituted or unsubstituted alkyl, substituted or unsubstituted haloalkyl, or substituted or unsubstituted polyether; or where any of $R^1$, $R^2$, $R^3$, $R^4$, and $R^5$ is a linker to a polymer backbone, the linker may be absent, absent, alkylene, -alkyl-O-alkyl, or —CH$_2$CH$_2$OC(O)—, a carbonyl, or a, alkyl ester group. In some embodiments, $R^{10}$, $R^{11}$, $R^{12}$, $R^{13}$, $R^{14}$, $R^{15}$, $R^{16}$, $R^{17}$, $R^{18}$, and $R^{19}$ may be each independently H, C$_1$-C$_{10}$ alkyl, C$_1$-C$_{10}$ haloalkyl, or polyether. In some embodiments, $R^{10}$, $R^{11}$, $R^{12}$, $R^{13}$, $R^{14}$, $R^{15}$, $R^{16}$, $R^{17}$, $R^{18}$, and $R^{19}$ may be each independently H, methyl, ethyl, n-propyl, i-propyl, n-butyl, sec-butyl, tert-butyl, or polyether. In some embodiments, any of $R^{10}$, $R^{11}$, $R^{14}$, or $R^5$ may be a linker, L, to a polymer backbone, and L may be absent, alkylenyl, -alkyl-O-alkyl-, a carbonyl, or an alkyl ester group. In some embodiments, $R^{10}$ and $R^{11}$ are H, methyl, alkyl-O-alkyl, ethyl, or 2-methoxyethyl, and $R^{12}$ and $R^{13}$ are H. In some embodiments, $R^{14}$ and $R^{15}$ are H, methyl, alkyl-O-alkyl, ethyl, or 2-methoxyethyl, and $R^{16}$, $R^{17}$, $R^{18}$, and $R^{19}$ are H.

Some illustrative compounds for use in electrochemical devices include, but are not limited to:

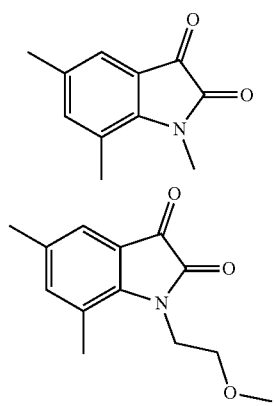

-continued
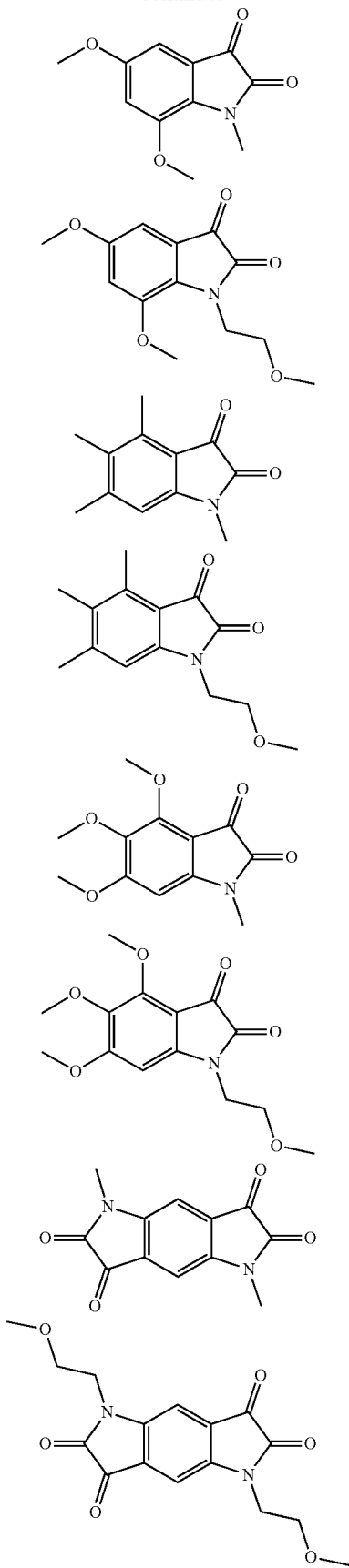
-continued
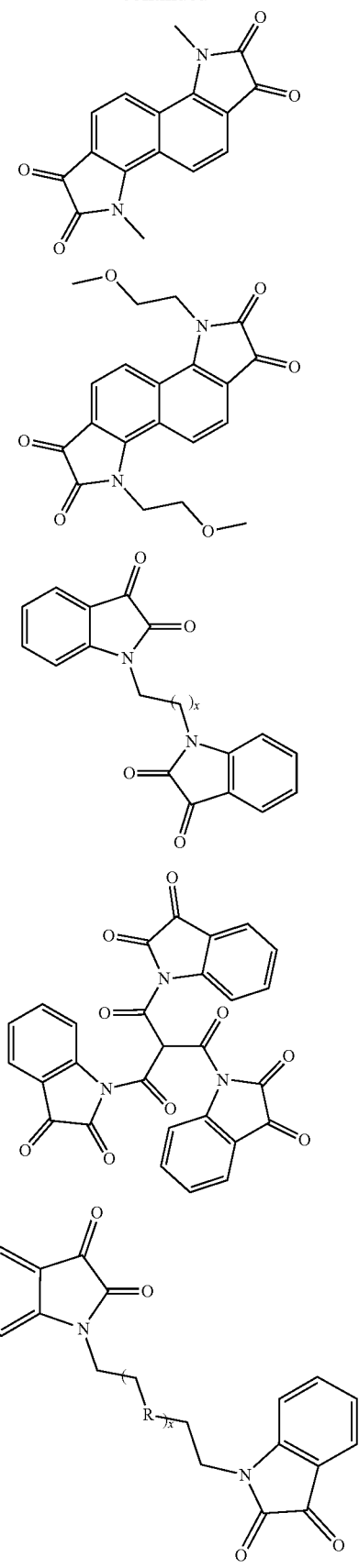

-continued

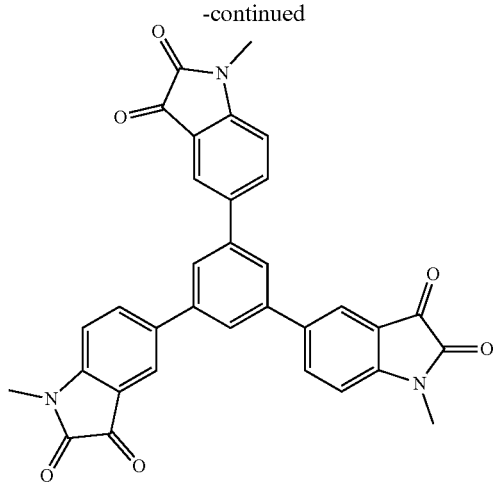

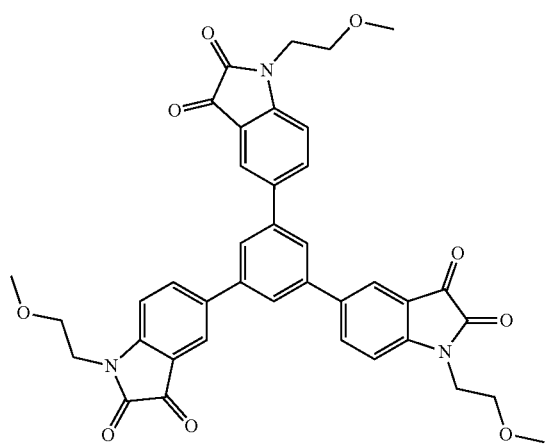

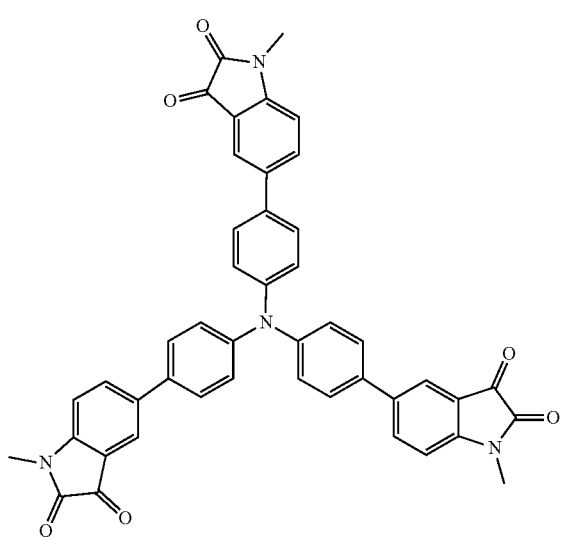

-continued

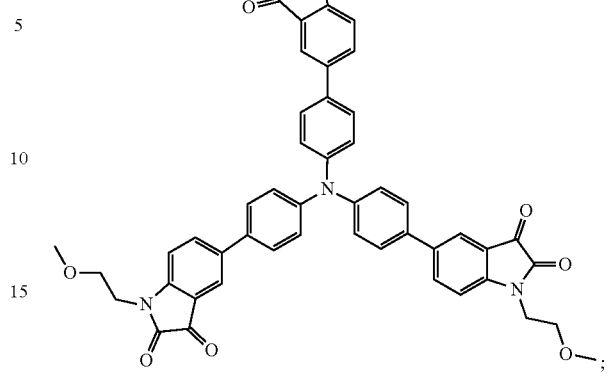

wherein x is from 0 to 25 and R is ethylene oxide, S, O, N-alkyl, or C=O.

In any of the above aspects or embodiments, the electrochemical device may be a redox flow battery or a lithium ion battery.

Redox Flow Batteries

Figure 7:
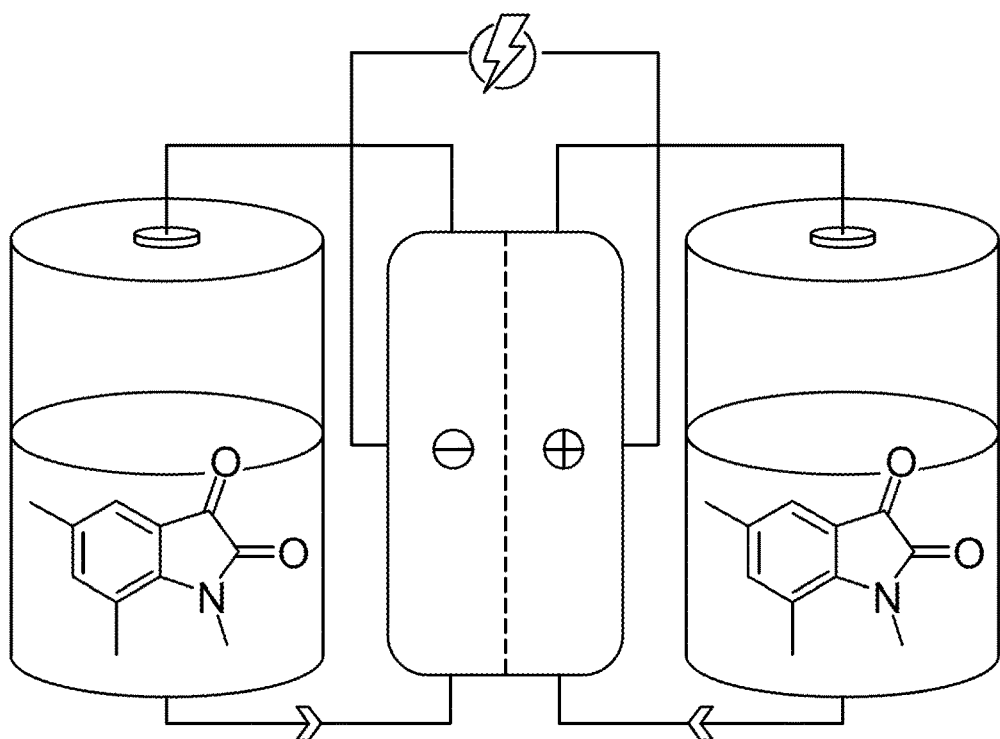
FIG. 7 is a schematic figure of a redox flow battery, according to various embodiments.

Redox flow batteries are electrochemical devices in which the anolyte (reducible active material) and the catholyte (oxidizable active material) are held in separated chambers as solution materials, typically dissolved in a solution. Each chamber may then be subject to a charging voltage to oxidize or reduce the respective species, wherein such charged species may then be stored in their active state until such a time as they a required. At that point, the solutions may then pumped or flowed from their respective anolyte or catholyte reservoirs (or chambers) to a reaction unit in which the catholyte is brought into close contact with the anolyte across a membrane where the redox process is carried out. The spent catholyte and anolyte may then be oxidized and reduced, respectively, back to their original state, for the process to be repeated. A schematic drawing of a redox flow battery is shown in FIG. 7, where the anolyte and catholytes are separately contained and can flow to the reaction chamber. In the illustrated schematic, 1,5,7-trimethylisatin is shown as both the catholyte and anolyte, where the catholyte is the positively biased compound and the anolyte is the negatively biased compound. Such use of the same compound is described as a "bipolar redox active material." The process of charging a redox flow battery is illustrated, using the trimethylisatin as an example, in FIG. 8, where the neutral species are converted to their charged states upon application a sufficient voltage.

Figure 8:
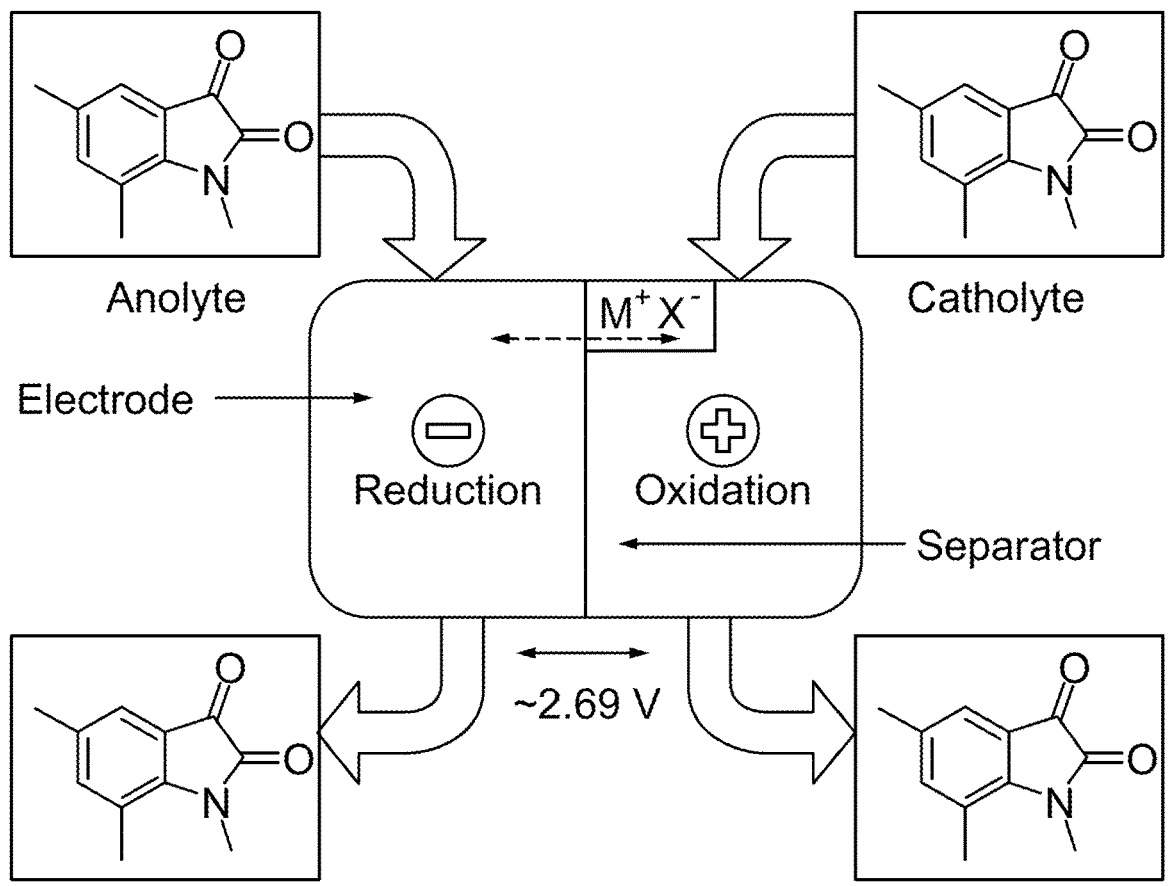
FIG. 8 is conceptual rendering of the chemical process of a redox flow battery, illustrating the change in redox state for an isatin derivative, according to various embodiments.

A bipolar redox active material is able to undergo oxidation as well as reduction reactions, and which therefore, could be applied as both the cathode and anode active material. This feature would ease the synthesis effort and potentially overcome the problems arise from active material crossover, since a slow mixing of the electrolytes would only lead to a reduced coulombic efficiency but not to a continuously declining charge/discharge capacity. FIG. 8 illustrates the processes at work in the redox flow battery during charging, while the reverse occurs (i.e. charged to neutral) during discharge of the redox flow battery.

The RFBs include a catholyte reservoir, an anolyte reservoir, a reaction chamber, a catholyte active material and a first non-aqueous solvent, and an anolyte active material and a second non-aqueous solvent, wherein the catholyte active material, the anolyte active material, or both catholyte active material and the anolyte active material include any of the compounds represented above as Formula I, V, VI, VII, or VIII. The catholyte and anolyte may also contain an electrolyte salt.

Illustrative salts for use in the batteries described herein, including the redox flow batteries and other metal ion batteries, include salts such as, but not limited to, tetrabutylammonium hexafluorophosphate ($[NBu_4][PF_6]$), tetrapropylammonium hexafluorophosphate ($[NPr_4][PF_6]$), tetraethylammonium hexafluorophosphate ($[NEt_4][PF_6]$), tetrabutylammonium tetrafluoroborate ($[NBu_4][BF_4]$), tetrapropylammonium tetrafluoroborate ($[NPr_4][BF_4]$), tetraethylammonium tetrafluoroborate ($[NEt_4][BF_4]$), tetrabutylammonium perchlorate ($[NBu_4][ClO_4]$), tetrapropylammonium perchlorate ($[NPr_4][ClO_4]$), tetraethylammonium perchlorate ($[NEt_4][ClO_4]$), tetrabutylammonium bis(trifluoromethansulfonyl)imide ($[NBu_4][TFSI]$), tetrapropylammonium bis(trifluoromethansulfonyl)imide ($[NPr_4][TFSI]$), tetraethylammonium bis(trifluoromethansulfonyl)imide ($[NEt_4][TFSI]$), lithium bis(trifluoromethansulfonyl)imide (Li[TFSI]), sodium bis(trifluoromethansulfonyl)imide (Na[TFSI]), potassium hexafluorophosphate ($K[PF_6]$), and potassium tetrafluoroborate ($K[BF_4]$). Other illustrative electrolyte salts include $NaClO_4$, $NaPF_6$, $NaAsF_6$, $NaBF_4$, $NaCF_3SO_3$, $NaN(SO_2CF_3)$, $LiClO_4$, $LiPF_6$, $LiAsF_6$, $LiBF_4$, $LiCF_3SO_3$, or $LiN(SO_2CF_3)$, or any combination thereof. The salt may be present in the electrolyte at a concentration of about 0.01 M to about 3.0 M. This includes a concentration of about 0.01 M to about 2.5 M, about 0.01 M to about 2.0 M, about 0.01 M to about 2.0 M, about 0.01 M to about 1.5 M, about 0.01 M to about 1.0 M, about 0.01 M to about 0.5 M, or about 0.01 M to about 0.1 M. In some embodiments, the salt is present in the electrolyte at a concentration of about 0.5 M to about 3.0 M. This includes a concentration of about 0.5 M to about 2.0 M, about 0.5 M to about 1.5 M, about 1.0 M to about 3.0 M, or about 1.0 M to about 2.0 M. In some embodiments, the salt is present in the electrolyte at a concentration of about 0.01, 0.05, 0.1, 0.5, 1.0, 1.5, 2.0, 2.5, or 3.0 M, including increments therein.

Illustrative non-aqueous solvents that may be used in the RFBs include, but are not limited to, ethylene carbonate, dimethyl carbonate, ethyl methyl carbonate, diethyl carbonate, propylene carbonate, fluorinated carbonates, fluoroethylene carbonate, 4-(trifluoromethyl)-1,3-dioxolan-2-one, propylene carbonate, dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, dimethoxyethane, triglyme, dimethyl ether, diglyme, tetraglyme, dimethyl ethylene carbonate, ethyl acetate, trifluoroethyl acetate, ethyl methyl sulfone, sulfolane, methyl isopropyl sulfone, butyrolactone, acetonitrile, succinonitrile, methyl 2-cyanoacetate, N,N-dimethylacetamide, 2,2,2-trifluoro-N,N-dimethylacetamide, methyl dimethylcarbamate, 2,2,2-trifluoroethyl dimethylcarbamate, or a mixture of any two or more thereof. Other solvents that may be used in the electrolytes include, but are not limited to, organic sulfates, esters, cyclic esters, fluorinated esters, nitriles, amides, dinitriles, fluorinated amides, carbamates, fluorinated carbamates, cyanoester compounds, and ionic liquid such as pyrrolidinium-based ionic liquids, piperidinium-based ionic liquids, imidazolium-based ionic liquids, ammonium-based ionic liquids, phosphonium-based ionic liquids, cyclic phosphonium-based ionic liquids, and sulfonium-based ionic liquids. In some embodiments, the solvents are ether-based solvents. Illustrative ether-based solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra (ethylene glycol) dimethyl ether ("TEGDME"), poly (ethylene glycol) dimethyl ether (PEGDME), (2,2,2-trifluoroethyl) carbonate (FEMC), 1,4-dioxane, 1,1,2,2-tetrafluoroethyl-2,2,3,3-tetrafluoropropyl ether; 1,1,2,2-tetrafluoroethyl-2,2,3,3-pentafluoropropyl ether; 2,2,2-trisfluoroethyl-1,1,2,3,3,3-hexafluoropropyl ether; ethyl-1,1,2,3,3,3-hexafluoropropyl ether; difluoromethyl-2,2,3,3,3-pentafluoropropyl ether; difluoromethyl-2,2,3,3-tetrafluoropropyl ether; 2-fluoro-1,3-dioxolane; 2,2-difluoro-1,3-dioxolane; 2-trifluoromethyl-1,3-dioxolane; 2,2-bis(trifluoromethyl)-1,3-dioxolane; 4-fluoro-1,3-dioxolane; 4,5-difluoro-1,3-dioxolane, or a mixture of any two or more. In some embodiments, the solvents may be carbonated-based solvents, ether-based solvents, fluorinated ether-based solvents, dimethyl sulfoxide, sulfone, ionic liquids, or a mixture of any two or more thereof. In some embodiments, the non-aqueous solvents are non-fluorinated, non-aqueous solvents. Illustrative non-fluorinated, non-aqueous solvents include, but are not limited to, ethylene carbonate, dimethyl carbonate, ethyl methyl carbonate, diethyl carbonate, propylene carbonate, fluorinated carbonate, or a mixture of any two or more thereof. In some embodiments, the co-solvents are ether-based solvents. Illustrative ether-based co-solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra(ethylene glycol) dimethyl ether ("TEGDME"), poly (ethylene glycol) dimethyl ether (PEGDME), 1,4-dioxane, or a mixture of any two or more thereof. Illustrative fluorinated solvents include, but are not limited to, fluorinated carbonates, fluorinated ethers, fluorinated esters, fluorinated amides, and fluorinated carbamates. Non-limiting examples include, but are not limited to, fluoroethylene carbonate, difluoroethylene carbonate, 4-(trifluoromethyl)-1,3-dioxolan-2-one, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, trifluoroethyl acetate, 2,2,2-trifluoro-N,N-dimethylacetamide, 2,2,2-trifluoroethyl dimethylcarbamate, or a mixture of any two or more thereof.

In another aspect, an electrochemical device is provided that includes a catholyte reservoir containing a catholyte material dissolved in a first non-aqueous solvent, an anolyte reservoir containing an anolyte material dissolved in a second non-aqueous solvent; and a reaction chamber, wherein the electrochemical device is a redox flow battery. In such a flow battery, the first and second non-aqueous solvents may be the same or different. In such flow batteries, the catholyte material, the anolyte material, or both the catholyte material and the anolyte material may be an isatin derivative compound. As used herein, "an isatin derivative compound," is a one based upon isatin, and in the broadest sense includes isatin, unless isatin is specifically exempted by structure or name.

In some embodiments of the redox flow battery, the isatin derivative compound may be other than isatin and/or 5-methylisatin. In other embodiments, the isatin derivative is a compound represented by Formula I.

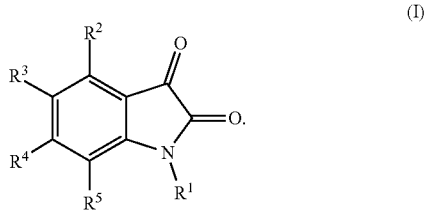

(I)

In redox flow batteries that include the compound of Formula I, $R^1$, $R^2$, $R^3$, $R^4$, and $R^5$ may be each independently H, substituted or unsubstituted alkyl, substituted or unsubstituted haloalkyl, substituted or unsubstituted aryl, or substituted or unsubstituted polyether; or where any of $R^1$, $R^2$, $R^3$, $R^4$, and $R^5$ is a linker to a polymer backbone, where the linker is absent, aryl-E, E-aryl, a carbonyl, alkylene, -alkyl-O-alkyl, or a alkyl ester, wherein E is an alkylene or alkyl-O-alkyl. In some embodiments, E is $CH_2$. In some embodiments, at least one of $R^1$, $R^2$, $R^3$, $R^4$, and $R^5$ is other than H. In any such embodiments, when $R^1$ is H, $R^3$ may be other than methyl.

In some embodiments of the redox flow battery, the catholyte and anolyte materials are both the isatin derivative. In some embodiments of the redox flow battery, the first and the second non-aqueous solvents are the same.

Lithium Ion Batteries

In another aspect, a lithium ion battery is provided that includes an anode, a cathode, a separator disposed between the anode and cathode, an electrolyte including a non-aqueous solvent, a salt, and a redox shuttle that includes any of the compounds represented above as Formula I, V, VI, VII, or VIII.

Illustrative non-aqueous solvents that may be used in the RFBs include, but are not limited to, ethylene carbonate, dimethyl carbonate, ethyl methyl carbonate, diethyl carbonate, propylene carbonate, fluorinated carbonates, fluoroethylene carbonate, 4-(trifluoromethyl)-1,3-dioxolan-2-one, propylene carbonate, dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, dimethoxyethane, triglyme, dimethyl ether, diglyme, tetraglyme, dimethyl ethylene carbonate, ethyl acetate, trifluoroethyl acetate, ethyl methyl sulfone, sulfolane, methyl isopropyl sulfone, butyrolactone, acetonitrile, succinonitrile, methyl 2-cyanoacetate, N,N-dimethylacetamide, 2,2,2-trifluoro-N,N-dimethylacetamide, methyl dimethylcarbamate, 2,2,2-trifluoroethyl dimethylcarbamate, or a mixture of any two or more thereof. Other solvents that may be used in the electrolytes include, but are not limited to, organic sulfates, esters, cyclic esters, fluorinated esters, nitriles, amides, dinitriles, fluorinated amides, carbamates, fluorinated carbamates, cyanoester compounds, and ionic liquid such as pyrrolidinium-based ionic liquids, piperidinium-based ionic liquids, imidazolium-based ionic liquids, ammonium-based ionic liquids, phosphonium-based ionic liquids, cyclic phosphonium-based ionic liquids, and sulfonium-based ionic liquids. In some embodiments, the solvents are ether-based solvents. Illustrative ether-based solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra (ethylene glycol) dimethyl ether ("TEGDME"), poly (ethylene glycol) dimethyl ether (PEGDME), (2,2,2-trifluoroethyl) carbonate (FEMC), 1,4-dioxane, 1,1,2,2-tetrafluoroethyl-2,2,3,3-tetrafluoropropyl ether; 1,1,2,2-tetrafluoroethyl-2,2,3,3,3-pentafluoropropyl ether; 2,2,2-trisfluoroethyl-1,1,2,3,3,3-hexafluoropropyl ether; ethyl-1,1,2,3,3,3-hexafluoropropyl ether; difluoromethyl-2,2,3,3,3-pentafluoropropyl ether; difluoromethyl-2,2,3,3-tetrafluoropropyl ether; 2-fluoro-1,3-dioxolane; 2,2-difluoro-1,3-dioxolane; 2-trifluoromethyl-1,3-dioxolane; 2,2-bis(trifluoromethyl)-1,3-dioxolane; 4-fluoro-1,3-dioxolane; 4,5-difluoro-1,3-dioxolane, or a mixture of any two or more. In some embodiments, the solvents may be carbonated-based solvents, ether-based solvents, fluorinated ether-based solvents, dimethyl sulfoxide, sulfone, ionic liquids, or a mixture of any two or more thereof. In some embodiments, the non-aqueous solvents are non-fluorinated, non-aqueous solvents. Illustrative non-fluorinated, non-aqueous solvents include, but are not limited to, ethylene carbonate, dimethyl carbonate, ethyl methyl carbonate, diethyl carbonate, propylene carbonate, fluorinated carbonate, or a mixture of any two or more thereof. In some embodiments, the co-solvents are ether-based solvents. Illustrative ether-based co-solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra(ethylene glycol) dimethyl ether ("TEGDME"), poly (ethylene glycol) dimethyl ether (PEGDME), 1,4-dioxane, or a mixture of any two or more thereof. Illustrative fluorinated solvents include, but are not limited to, fluorinated carbonates, fluorinated ethers, fluorinated esters, fluorinated amides, and fluorinated carbamates. Non-limiting examples include, but are not limited to, fluoroethylene carbonate, difluoroethylene carbonate, 4-(trifluoromethyl)-1,3-dioxolan-2-one, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, trifluoroethyl acetate, 2,2,2-trifluoro-N,N-dimethylacetamide, 2,2,2-trifluoroethyl dimethylcarbamate, or a mixture of any two or more thereof.

The cathode may include an cathode active material, a binder, and a current collector. The cathode active material may include a lithium transition metal oxide or a sodium transition metal oxide. For example, the cathode active material may include a spinel, an olivine, a surface modified olivine $LiFePO_4$, $LiMn_{0.5}Ni_{0.5}O_2$, $LiCoO_2$, $LiNiO_2$, $LiNi_{1-x}Co_yMe_zO_2$, $LiNi_\alpha Mn_\beta Co_\gamma O_2$, $LiMn_2O_4$, $LiFeO_2$, $LiNi_{0.5}Me^1_{1.5}O_4$, $Li_{1+x'}Ni_hMn_kCo_lMe^2_{y'}O_{2-z'}F_{z'}$, $VO_2$, $E_{x''}F_2(Me_3O_4)_3$, or $LiNi_mMn_nO_4$, wherein Me is Al, Mg, Ti, B, Ga, Si, Mn, or Co; $Me^2$ is Mg, Zn, Al, Ga, B, Zr, or Ti; E is Li, Ag, Cu, Na, Mn, Fe, Co, Ni, or Zn; F is Ti, V, Cr, Fe, or Zr; wherein $0 \leq x \leq 0.3$; $0 \leq y \leq 0.5$; $0 \leq z \leq 0.5$; $0 \leq m \leq 2$; $0 \leq n \leq 2$; $0 \leq x' \leq 0.4$; $0 \leq \alpha \leq 1$; $0 \leq \beta \leq 1$; $0 \leq \gamma \leq 1$; $0 \leq h \leq 1$; $0 \leq k \leq 1$; $0 \leq l \leq 1$; $0 \leq y' \leq 0.4$; $0 \leq z' \leq 0.4$; and $0 \leq x'' \leq 3$; with the proviso that at least one of h, k and l is greater than 0. The term "spinel" refers to a manganese-based spinel such as, $Li_{1+x}Mn_{2-}$ $_yMe_zO_{4-h}A_k$, wherein Me is Al, Mg, Ti, B, Ga, Si, Ni, or Co; A is S or F; and wherein $0 \leq x \leq 0.5$, $0 \leq y \leq 0.5$, $0 \leq z \leq 0.5$, $0 \leq h \leq 0.5$, and $0 \leq k \leq 0.5$. The term "olivine" refers to an iron-based olivine such as, $LiFe_{1-x}Me_yPO_{4-h}A_k$, wherein Me is Al, Mg, Ti, B, Ga, Si, Ni, or Co; A is S or F; and wherein $0 \leq x \leq 0.5$, $0 \leq y \leq 0.5$, $0 \leq h \leq 0.5$, and $0 \leq k \leq 0.5$.

In some embodiments, the cathode active material includes a layered structure, a spinel, a olivine with and without coating material that includes, but is not limited to carbon, polymer, fluorine, metal oxides, $NaFePO_4$, $NaCoO_2$, $NaNiO_2$, $NaMn_2O_4$, or $Na_{1-x}Ni_\alpha Co_\beta Mn_\gamma M_\delta)_{2-z}N_z$, wherein M is Li, Al, Mg, Ti, B, Ga, Si, Zr, Zn, Cu, Fe; N is F, Cl, S; wherein $0 \leq x \leq 1$, $0 \leq \alpha \leq 1$, $0 \leq \beta \leq 1$, $0 \leq \gamma \leq 1$, $0 \leq \delta \leq 1$, $0 \leq z \leq 2$; with the proviso that at least one of $\alpha$, $\beta$ and $\gamma$ is greater than 0. In some embodiments, the positive electrode includes $Li_{1+w}Mn_xNi_yCo_zO_2$ wherein w, x, y, and z satisfy the relations $0 \leq w < 1$, $0 \leq x < 1$, $0 \leq y < 1$, $0 \leq z < 1$, and $x+y+z=1$. In some embodiments, the cathode active material may be intercalated with lithium.

In some embodiments, the cathode active material includes $LiMn_xNi_yO_4$ wherein x and y satisfy $0 \leq x < 2$, $0 \leq y < 2$, and $x+y=2$. In some embodiments, the cathode includes $LiMn_xNi_yO_4$ wherein x and y satisfy $0 \leq x < 2$, $0 \leq y < 2$, and $x+y=2$. In some embodiments, the cathode includes $xLi_2MnO_3 \cdot (1-x)LiMO_2$ is wherein $0 \leq x < 2$. In some embodiments, the cathode active material includes $Na_wMn_xNi_yCo_zO_2$ wherein w, x, y, and z satisfy the relations $0 < w < 1.5$, $0 \leq x < 1$, $0 \leq y < 1$, $0 \leq z < 1$, and $x+y+z=1$. In some embodiments, the cathode includes $Na_wMe_xO_2$ wherein Me is any transition metal and w and x satisfy the relations $0 < w < 1.5$, $0 \leq x < 1$.

The cathode active material may be further stabilized by surface coating the active particles with a material that can neutralize acid or otherwise lessen or prevent leaching of the transition metal ions. For example, the cathode active materials may include a surface coating of a metal oxide or fluoride such as $ZrO_2$, $TiO_2$, $ZnO_2$, $WO_3$, $Al_2O_3$, $MgO$, $SiO_2$, $SnO_2$, $AlPO_4$, $Al(OH)_3$, $AlF_3$, $ZnF_2$, $MgF_2$, $TiF_4$, $ZrF_4$, $LiMPO_4$ or $LiMBO_3$, where in M indicates transition metal such as but not limited to Ni, Mn, Co, a mixture of any two or more thereof, or any other suitable metal oxide or fluoride. The coating can be applied to a carbon-coated cathode.

The cathode active material may be further stabilized by surface coating the active particles with polymer materials. Examples of polymer coating materials include, but not limited to, polysiloxanes, polyethylene glycol, or poly(3,4-ethylenedioxythiophene)polystyrene sulfonate, a mixture of any two or more polymers.

The cathode may also include conductive carbon materials in addition to the active material and the binders. Illustrative conductive carbon materials for use in the cathode include, but are not limited to, synthetic graphite, natural graphite, expanded graphite, graphene, reduced graphene oxide, a metal-organic framework, amorphous carbon, hard carbon, soft carbon, carbon black, acetylene black, carbon spheres, mesocarbon microbeads (MCMB), mesoporous carbon, porous carbon matrix, carbon nanofiber, carbon aerogel, single-walled carbon nanotubes, multi-walled carbon nanotubes, carbon nanotube arrays, and any mixture of two or more thereof. In some embodiments, the conductive carbon materials include, microporous carbon, mesoporous carbon, mesoporous microbeads, graphite, expandable graphite, carbon black, or carbon nanotubes, or any combination thereof. Commercial examples of carbon black include, but are not limited to, Super P®, Black Pearls® 2000, Denka Black®, Vulcan XC72R®, and Ketjen Black®. In some embodiments, the conductive carbon material includes synthetic graphite, natural graphite, expanded graphite, graphene, reduced graphene oxide, a metal-organic framework, amorphous carbon, hard carbon, soft carbon, carbon black, acetylene black, carbon spheres, mesocarbon microbeads (MCMB), mesoporous carbon, porous carbon matrix, carbon nanofiber, carbon aerogel, single-walled carbon nanotubes, multi-walled carbon nanotubes, carbon nanotube arrays, or any mixture of two or more thereof.

The anode may include an anode active material, a binder, and a current collector. Illustrative anode active materials that may be used in the lithium ion batteries include, but are not limited to, natural graphite, synthetic graphite, hard carbon, amorphous carbon, soft carbon, mesocarbon microbeads (MCMB), acetylene black, Ketjen® black, carbon black, mesoporous carbon, porous carbon matrix, carbon nanotube, carbon nanofiber, graphene, silicon microparticle, silicon nanoparticle, silicon-carbon composite, tin microparticle, tin nanoparticle, tin-carbon composite, silicon-tin composite, phosphorous-carbon composites, black phosphorus, red phosphorus, mixture of red and black phosphorus, lithium titanium oxide, lithium metal, sodium metal, lithium titanium oxide or magnesium metal. In some embodiments, the anode includes synthetic graphite, natural graphite, amorphous carbon, hard carbon, soft carbon, acetylene black, MCMB, carbon black, Ketjen® black, mesoporous carbon, porous carbon matrix, carbon nanotube, carbon nanofiber, graphene, black phosphorus, red phosphorus, mixture of red and black phosphorus, Ge, SnSb, $NiCo_2O_4$, $Sb_2O_4$, or $Co_3O_4$. In some embodiments, the anode may include a carbon-based material that is intercalated with lithium or sodium, or is alloyed with lithium or sodium metal. In some embodiments, the anode is comprised of particles of the described materials, and the particles are microparticles or nanoparticles. In some embodiments, the negative electrode includes hard carbon or phosphorus-carbon composites or sodium metal or organosodium compound. In some embodiments, the particles are microparticles or nanoparticles.

The anode active material may be further stabilized by surface coating the active particles with a material. Hence the anodes can also comprise a surface coating of a metal oxide or fluoride such as $ZrO_2$, $TiO_2$, $ZnO_2$, $WO_3$, $Al_2O_3$, $MgO$, $SiO_2$, $SnO_2$, $AlPO_4$, $Al(OH)_3$, $AlF_3$, $ZnF_2$, $MgF_2$, $TiF_4$, $ZrF_4$, a mixture of any two or more thereof, of any other suitable metal oxide or fluoride.

The anode active material may be further stabilized by surface coating the active particles with polymer materials. Examples of polymer coating materials include, but not limited to, polysiloxanes, polyethylene glycol, or poly(3,4-ethylenedioxythiophene)polystyrene sulfonate, a mixture of any two or more polymers.

Illustrative current collectors for either the anode or the cathode may be any of a wide variety of materials. For example, illustrative current collectors include, but are not limited to, copper, stainless steel, titanium, tantalum, platinum, palladium, gold, silver, iron, aluminum, nickel, rhodium, manganese, vanadium, titanium, tungsten, cobalt nickel alloy, highly alloyed ferritic stainless steel containing molybdenum and chromium; or nickel-, chromium-, or molybdenum-containing alloys, or a carbon-coated metal described above. The current collector may take the form of a foil, mesh, or screen. In some embodiments, the electroactive material disclosed herein and one or more of a conductive carbon material and a binder are contacted with the current collector by casting, pressing, or rolling the mixture thereto. In some embodiments, the current collector is copper, stainless steel, titanium, tantalum, platinum, gold, aluminum, nickel, cobalt, cobalt nickel alloy, highly alloyed ferritic stainless steel containing molybdenum and chromium, a nickel-containing alloy, a chromium-containing alloy, or a molybdenum-containing alloy.

When used, the binder for the cathode may be present in the electrode in an amount of from about 0.1 wt % to about 99 wt %. In some embodiments, the binder is present in the electrode in an amount of from about 2 wt % to about 20 wt %. Illustrative binders include, but are not limited to, polyvinylidene fluoride (PVDF), polyvinyl alcohol (PVA), polyethylene, polystyrene, polyethylene oxide, polytetrafluoroethylene (Teflon), polyacrylonitrile, polyimide, styrene butadiene rubber (SBR), carboxy methyl cellulose (CMC), gelatine, sodium alginate, polythiophene, polyacetylene, poly(9,9-dioctylfluorene-co-fluorenone), poly(9,9-dioctylfluorene-co-fluorenone-co-methylbenzoic ester), a copolymer of any two or more such polymers, and a blend of any two or more such polymers. In some embodiments, the binder is an electrically conductive polymer such as, but not limited to, polythiophene, polyacetylene, poly(9,9-dioctylfluorene-co-fluorenone), poly(9,9-dioctylfluorene-co-fluorenone-co-methylbenzoic ester), and a copolymer of any two or more such conductive polymers. In some embodiments, the binder includes polyaniline, polypyrrole, poly(pyrrole-co-aniline), polyphenylene, polythiophene, polyacetylene, polysiloxane, polyvinylidene difluoride (PVDF), polyfluorene, polyvinyl alcohol (PVA), polyethylene, polystyrene, polyethylene oxide, polytetrafluoroethylene (Teflon), polyacrylonitrile, polyimide, styrene butadiene rubber (SBR), carboxy methyl cellulose (CMC), alginate, gelatine, a copolymer of any two or more such polymers, or a blend of any two or more such polymers.

In some embodiments, the electrolyte includes a lithium salt and a solvent. The lithium salt may be $LiClO_4$, $LiPF_6$, $LiAsF_6$, $LiBF_4$, $LiCF_3SO_3$, or $LiN(SO_2CF_3)$, or any combination thereof. The salt may be present in the electrolyte at a concentration of about 0.01 M to about 3.0 M. This includes a concentration of about 0.01 M to about 2.5 M, about 0.01 M to about 2.0 M, about 0.01 M to about 2.0 M, about 0.01 M to about 1.5 M, about 0.01 M to about 1.0 M, about 0.01 M to about 0.5 M, or about 0.01 M to about 0.1 M. In some embodiments, the salt is present in the electrolyte at a concentration of about 0.5 M to about 3.0 M. This includes a concentration of about 0.5 M to about 2.0 M, about 0.5 M to about 1.5 M, about 1.0 M to about 3.0 M, or about 1.0 M to about 2.0 M. In some embodiments, the salt is present in the electrolyte at a concentration of about 0.01, 0.05, 0.1, 0.5, 1.0, 1.5, 2.0, 2.5, or 3.0 M, including increments therein.

In some embodiments, the electrolyte includes a sodium salt and a solvent. The sodium salt may be $NaClO_4$, $NaPF_6$, $NaAsF_6$, $NaBF_4$, $NaCF_3SO_3$, or $NaN(SO_2CF_3)$, or any combination thereof. The salt may be present in the electrolyte at a concentration of about 0.01 M to about 3.0 M. This includes a concentration of about 0.01 M to about 2.5 M, about 0.01 M to about 2.0 M, about 0.01 M to about 2.0 M, about 0.01 M to about 1.5 M, about 0.01 M to about 1.0 M, about 0.01 M to about 0.5 M, or about 0.01 M to about 0.1 M. In some embodiments, the salt is present in the electrolyte at a concentration of about 0.5 M to about 3.0 M. This includes a concentration of about 0.5 M to about 2.0 M, about 0.5 M to about 1.5 M, about 1.0 M to about 3.0 M, or about 1.0 M to about 2.0 M. In some embodiments, the salt is present in the electrolyte at a concentration of about 0.01, 0.05, 0.1, 0.5, 1.0, 1.5, 2.0, 2.5, or 3.0 M, including increments therein.

The non-aqueous solvent may include any solvents suitable for use in a lithium or sodium ion battery. Illustrative non-aqueous solvents include, but are not limited to, but are not limited to ethylene carbonate, dimethyl carbonate, ethyl methyl carbonate, diethyl carbonate, propylene carbonate, fluorinated carbonates, fluoroethylene carbonate, 4-(trifluoromethyl)-1,3-dioxolan-2-one, propylene carbonate, dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, dimethoxyethane, triglyme, dimethyl ether, diglyme, tetraglyme, dimethyl ethylene carbonate, ethyl acetate, trifluoroethyl acetate, ethyl methyl sulfone, sulfolane, methyl isopropyl sulfone, butyrolactone, acetonitrile, succinonitrile, methyl 2-cyanoacetate, N,N-dimethylacetamide, 2,2,2-trifluoro-N,N-dimethylacetamide, methyl dimethylcarbamate, 2,2,2-trifluoroethyl dimethylcarbamate, or a mixture of any two or more thereof. Other solvents that may be used in the electrolytes include, but are not limited to, organic sulfates, esters, cyclic esters, fluorinated esters, nitriles, amides, dinitriles, fluorinated amides, carbamates, fluorinated carbamates, cyanoester compounds, and ionic liquid such as pyrrolidinium-based ionic liquids, piperidinium-based ionic liquids, imidazolium-based ionic liquids, ammonium-based ionic liquids, phosphonium-based ionic liquids, cyclic phosphonium-based ionic liquids, and sulfonium-based ionic liquids. In some embodiments, the solvents are ether-based solvents. Illustrative ether-based solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra(ethylene glycol) dimethyl ether ("TEGDME"), poly (ethylene glycol) dimethyl ether (PEGDME), (2,2,2-trifluoroethyl) carbonate (FEMC), 1,4-dioxane, 1,1,2,2-tetrafluoroethyl-2,2,3,3-tetrafluoropropyl ether; 1,1,2,2-tetrafluoroethyl-2,2,3,3,3-pentafluoropropyl ether; 2,2,2-trisfluoroethyl-1,1,2,3,3,3-hexafluoropropyl ether; ethyl-1,1,2,3,3,3-hexafluoropropyl ether; difluoromethyl-2,2,3,3,3-pentafluoropropyl ether; difluoromethyl-2,2, 3,3-tetrafluoropropyl ether; 2-fluoro-1,3-dioxolane; 2,2-difluoro-1,3-dioxolane; 2-trifluoromethyl-1,3-dioxolane; 2,2-bis(trifluoromethyl)-1,3-dioxolane; 4-fluoro-1,3-dioxolane; 4,5-difluoro-1,3-dioxolane, or a mixture of any two or more. In some embodiments, the solvents may be carbonated-based solvents, ether-based solvents, fluorinated ether-based solvents, dimethyl sulfoxide, sulfone, ionic liquids, or a mixture of any two or more thereof. In some embodiments, the non-aqueous solvents are non-fluorinated, non-aqueous solvents. Illustrative non-fluorinated, non-aqueous solvents include, but are not limited to, ethylene carbonate, dimethyl carbonate, ethyl methyl carbonate, diethyl carbonate, propylene carbonate, fluorinated carbonate, or a mixture of any two or more thereof. In some embodiments, the co-solvents are ether-based solvents. Illustrative ether-based co-solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra(ethylene glycol) dimethyl ether ("TEGDME"), poly (ethylene glycol) dimethyl ether (PEGDME), 1,4-dioxane, or a mixture of any two or more thereof. Illustrative fluorinated solvents include, but are not limited to, fluorinated carbonates, fluorinated ethers, fluorinated esters, fluorinated amides, and fluorinated carbamates. Non-limiting examples include, but are not limited to, fluoroethylene carbonate, difluoroethylene carbonate, 4-(trifluoromethyl)-1,3-dioxolan-2-one, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, trifluoroethyl acetate, 2,2,2-trifluoro-N,N-dimethylacetamide, 2,2,2-trifluoroethyl dimethylcarbamate, or a mixture of any two or more thereof.

In some embodiments, the electrolyte further includes an electrolyte additive to enhance performance, or provide other desirable characteristics to the battery. Illustrative electrolyte additives include, but are not limited to, vinylene carbonate, fluorinated ethylene carbonated, cyclic disulfonic ester methylene methanedisulfonate (MMDS), lithium bis (oxolate)borate, sodium bis (oxolate)borate, potassium bis (oxolate)borate, ethylene sulfite, ethylene sulfate, trimethylene sulfite, 1,3-butylene glycol sulfite, tris(trimethylsilyl) phosphate (TMSP) and tris(trimethylsilyl)borate (TMSB). The electrolyte additive may be present in the electrolyte in an amount of about 1% to about 10% by weight or by volume. This includes an amount of about 1% to about 8% by weight or by volume, about 1% to about 6% by weight or by volume, about 1% to about 4% by weight or by volume, or about 1% to about 3% by weight or by volume. In some embodiments, the electrolyte additive is present in the electrolyte in an amount of about 1, 2, 3, 4, 5, 6, 7, 8, 0.9, or 10% by weight or by volume.

Illustrative separators for the batteries include, but are not limited to, Celgard® 2325 (a trilayer polypropylene/polyethylene/polypropylene separator), Celgard® 2400 (a polypropylene separator), Celgard® 3501 (a polypropylene separator), and glass fiber separators.

The present invention, thus generally described, will be understood more readily by reference to the following examples, which are provided by way of illustration and are not intended to be limiting of the present invention.

EXAMPLES

General Synthesis. Synthesis of substituted isatins may be carried out according to Scheme 1.

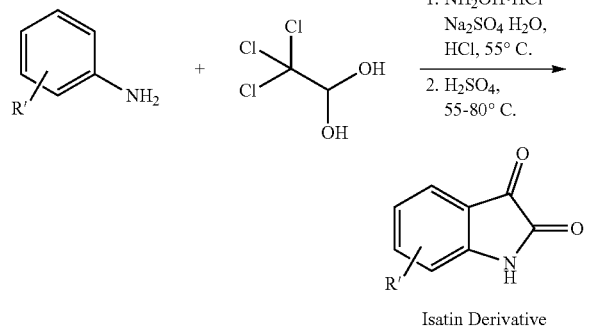

Isatin Derivative

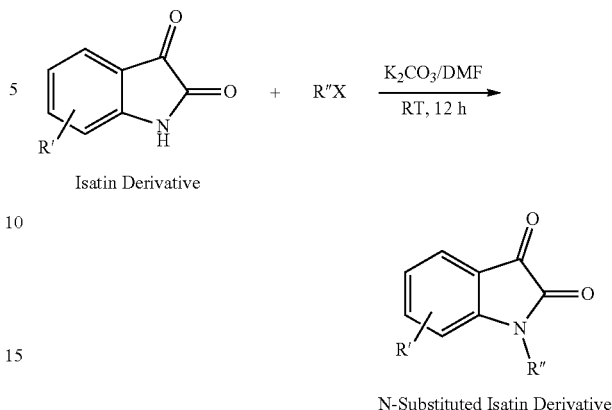

N-Substituted Isatin Derivative

Isatin derivatives can be synthesized by treating chloral hydrate (1.2 eq) with a suspension of hydroxylamine hydrochloride (3.5 eq), sodium sulfate (8 eq), and the appropriate aniline (1 eq) in water and 2 M aqueous hydrochloric acid at 55° C. overnight, with stirring. Followed by treating the intermediate hydroxyiminoacetanilide with a concentrated sulfuric acid at 55-80° C. to provide the isatin derivative. N-substituted isatin derivatives may be synthesized by treating the corresponding satin derivative with the appropriate halide in the presence of $K_2CO_3$ in DMF.

Example 1. Synthesis of 1,5,7-trimethylisatin

The compounds of the present application may be prepared according to the following generalized Scheme 2, and as illustrated below by the preparation of 1,5,7-trimethylisatin (Scheme 3).

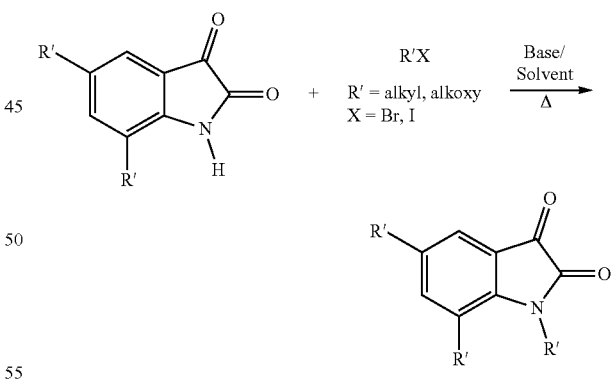

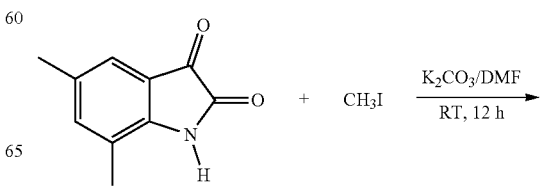

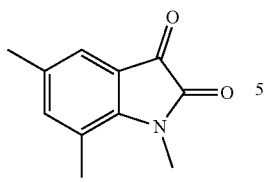

To a stirred solution of 5,7-dimethylisatin (5.3 g, 30.25 mmol) and $K_2CO_3$ (5 g, 36.3 mmol) in 30 mL DMF, was added methyl iodide (1.9 mL, 30.25 mmol) dropwise at room temperature and stirred overnight. After completion of the reaction the mixture was diluted with $CH_2Cl_2$ (100 mL), and water (50 mL). The organic layer was separated, and the aqueous phase was extracted with $CH_2Cl_2$ (2×50 mL). The combined organic layers were washed with saturated brine solution (100 mL) and dried over anhydrous $Na_2SO_4$ and concentrated under reduced pressure to give crude solid, which was purified by chromatography on a silica gel column (EtOAc/Hexane) to give 1,5,7-trimethylisatin as a red solid (2.8 g, 49% yield). $^1$H NMR (300 MHz, Chloroform-d) δ 7.24-7.18 (m, 1H), 7.16-7.09 (m, 1H), 3.45 (s, 3H), 2.49 (s, 3H), 2.24 (s, 3H). $^{13}$C NMR (75 MHz, Chloroform-d) δ 184.06, 159.30, 146.73, 142.79, 133.60, 123.66, 121.65, 118.51, 29.65, 20.38, 18.69.

Example 2. Synthesis of 1-(2-methoxyethyl)-5,7-dimethylindoline-2,3-dione (1-(2-methoxyethyl)-5,7-dimethylisatin) (Scheme 4)

Scheme 4

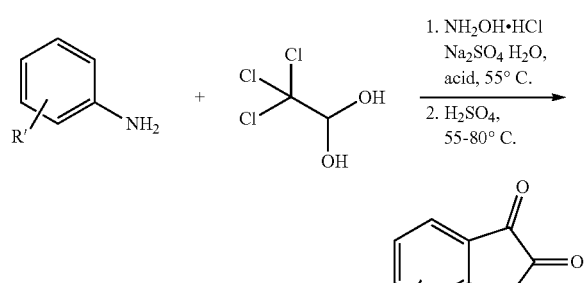

Isatin Derivative

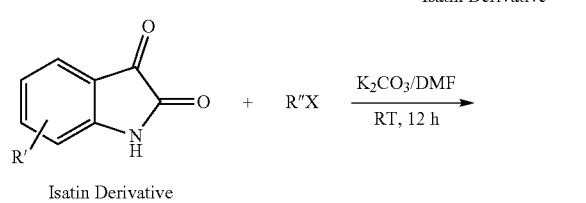

N-Substituted Isatin Derivative

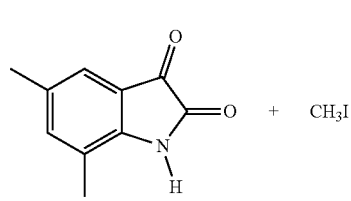

To a stirred solution of 5,7-dimethylisatin (5 g, 28.4 mmol) and $K_2CO_3$ (5.89 g, 42.6 mmol) in 30 mL DMF, was added 1-bromo-2-methoxyethane (2.94 mL, 31.3 mmol) dropwise at room temperature and stirred overnight at 40° C. After completion of the reaction the mixture was diluted with $CH_2Cl_2$ (100 mL), and water (50 mL). The organic layer was separated, and the aqueous phase was extracted with $CH_2Cl_2$ (2×50 mL). The combined organic layers were washed with saturated brine solution (100 mL) and dried over anhydrous $Na_2SO_4$ and concentrated under reduced pressure to give crude solid, which was purified by chromatography on a silica gel column (EtOAc/Hexane) to give 1-(2-methoxyethyl)-5,7-dimethylisatin as a red solid (1.3 g, 20% yield). $^1$H NMR (300 MHz, Chloroform-d) δ 7.26 (s, 1H), 7.13 (s, 1H), 4.12 (t, J=5.7 Hz, 2H), 3.62 (t, J=5.7 Hz, 2H), 3.32 (s, 3H), 2.48 (s, 3H), 2.26 (s, 3H).

Example 3. Cyclic Voltammetry of 1,5,7-Trimethylisatin in Acetonitrile ("MeCN" or "ACN")

Figure 3:
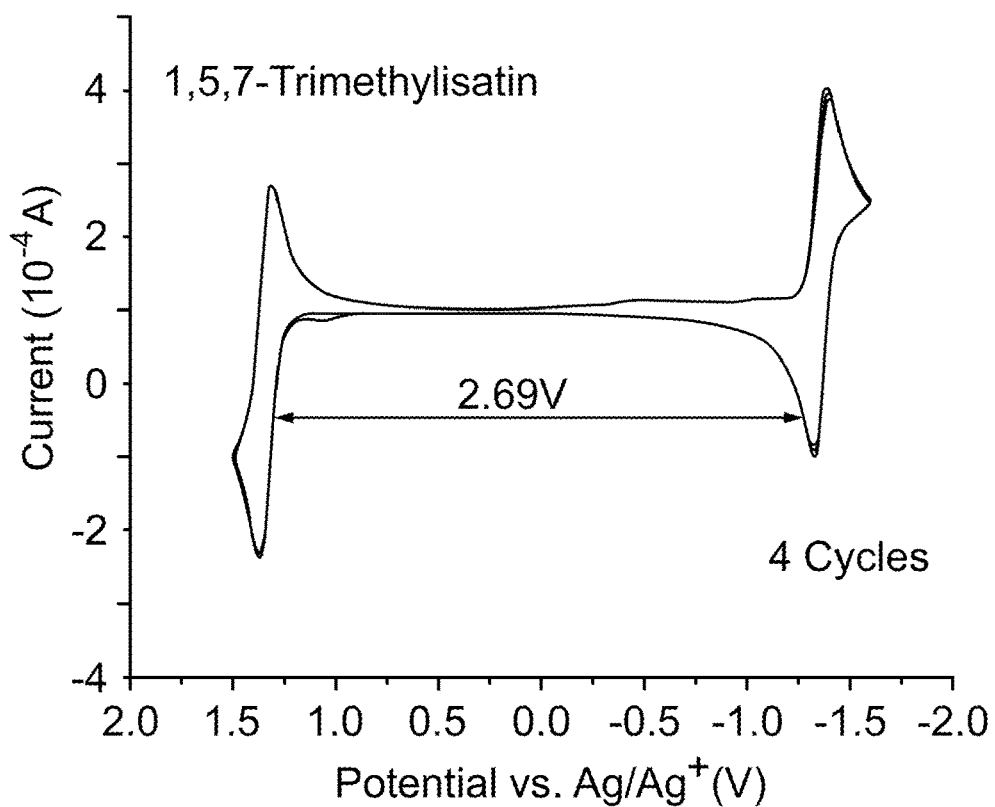
FIG. 3 is a full cyclic volatammetry scan for an acetonitrile solution of 1,5,7-trimethylisatin (10 mM) with TBAPF$_6$ (0.1 M), according to Example 23.
Figure 4:
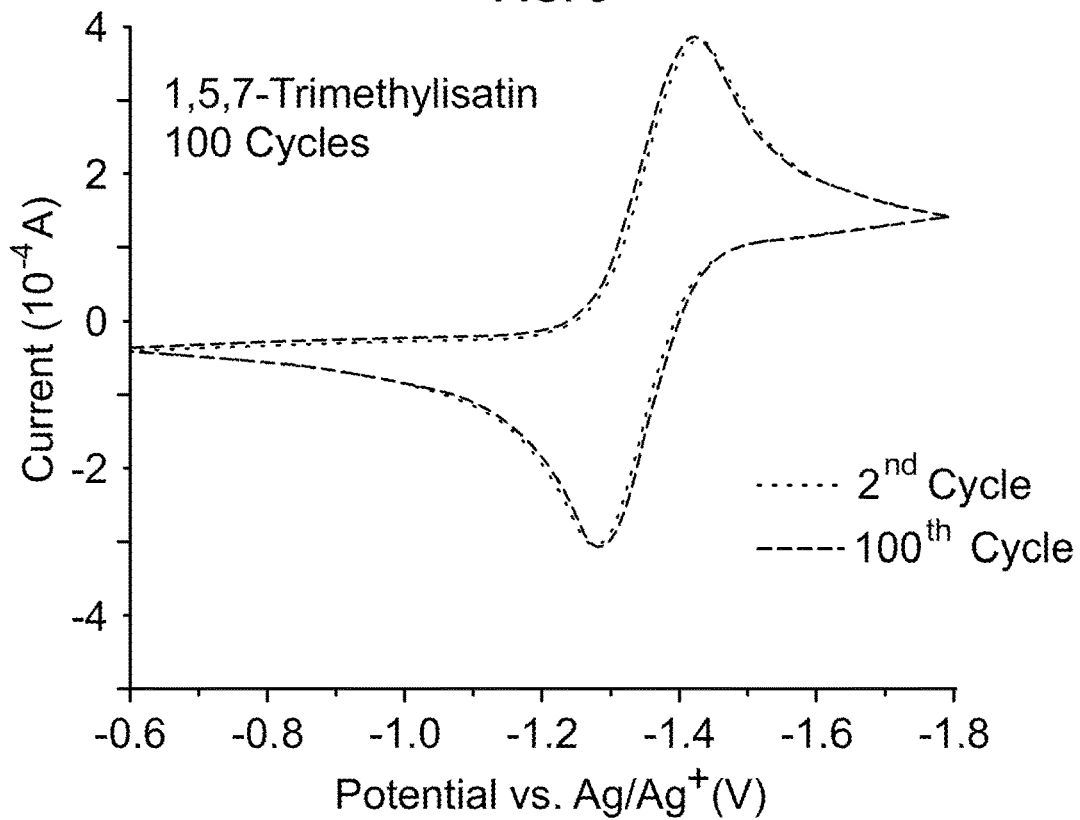
FIG. 4 illustrates the 2$^{nd}$ and 100$^{th}$ cyclic volatammetry scans in the negative direction, for an acetonitrile solution of 1,5,7-trimethylisatin (10 mM) with TBAPF$_6$ (0.1 M), at a scan rate of 100 mV/s, according to Example 3.
Figure 5:
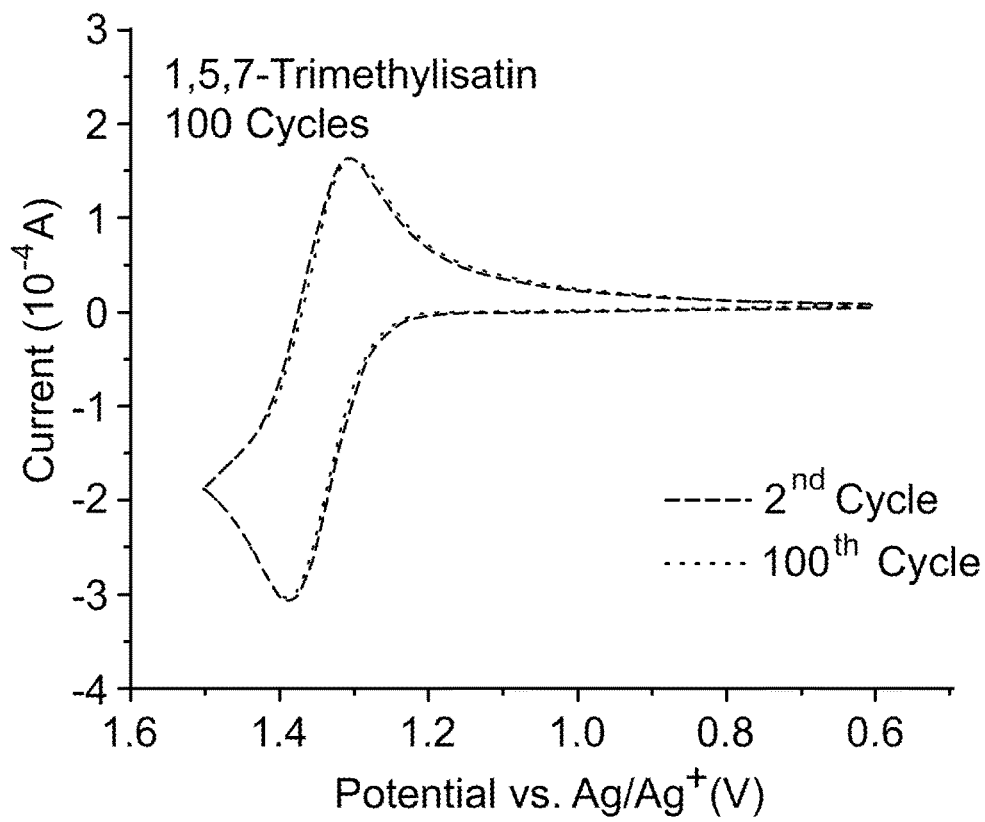
FIG. 5 illustrates the 2$^{nd}$ and 100$^{th}$ cyclic volatammetry scans in the positive direction, for an acetonitrile solution of 1,5,7-trimethylisatin (10 mM) with TBAPF$_6$ (0.1 M), at a scan rate of 100 mV/s, according to Example 3.

A solution of the 1,5,7-trimethylisatin (10 mM) in 0.1 M tetrabutylammonium hexafluorophosphate (TBAPF$_6$) in acetonitrile were prepared. Aliquots of the solution were then subjected to cyclic voltammetry using a three-electrode system of a glassy carbon working electrode, a platinum counter electrode, and a Ag/Ag$^+$ reference electrode, at different scan rates. As shown in FIG. 3 two redox couples were observed with redox potentials of about −1.35 V and about 1.34 V vs. Ag/Ag$^+$, with excellent reversibility. Even after 100 cycles at a cycle rates of 100 mV/s, the reversibility of redox process is very stable, as shown in FIGS. 4 and 5, where the 2$^{nd}$ and 100$^{th}$ cycles are shown to substantially overlap, indicating robust cyclability.

Example 4. Cyclic Voltammetry of 1,5,7-Trimethylisatin in Carbonate Solvents

Figure 6:
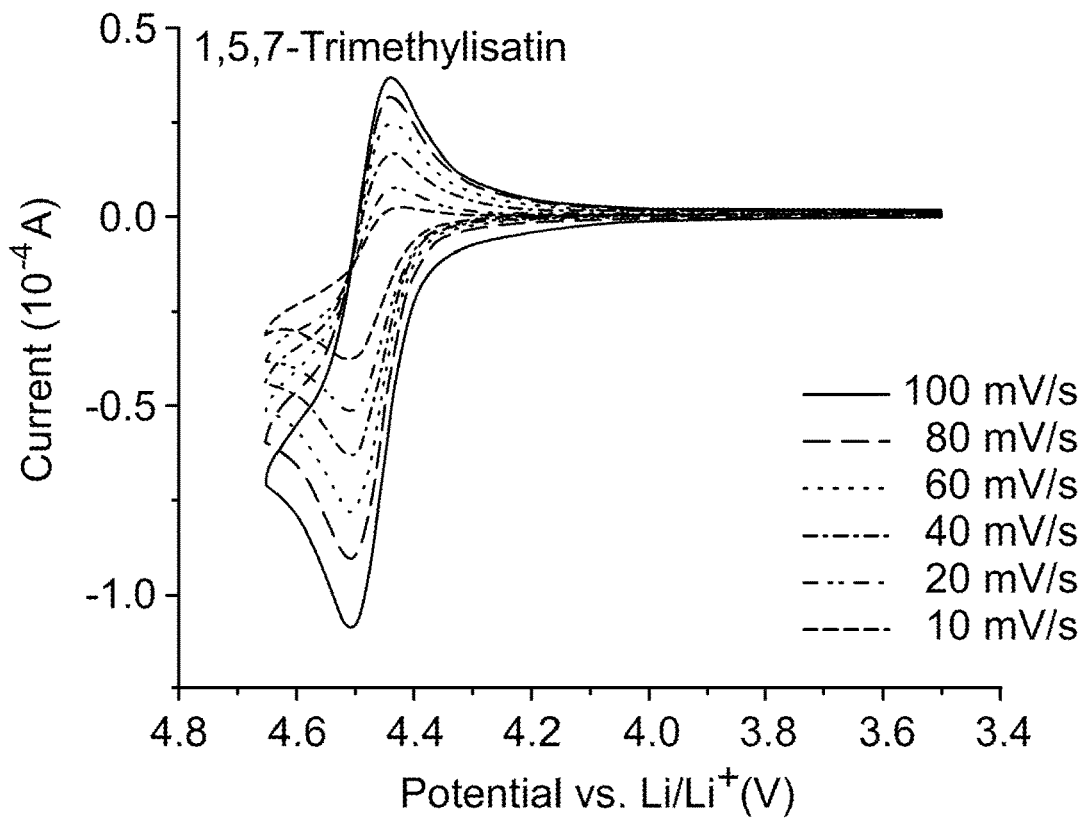
FIG. 6 illustrates cyclic volatammetry scans for a ethyl carbonate/ethylmethyl carbonate (3/7 weight basis) solution of 1,5,7-trimethylisatin (10 mM) with LiPF$_6$ (1.2 M), at different scan rates, according to Example 4.

A solution of the 1,5,7-trimethylisatin (10 mM) in 1.2 M lithium hexafluorophosphate (LiPF$_6$) in a 3/7 solution of ethyl carbonate/ethylmethyl carbonate, on a weight basis, were prepared. Aliquots of the solution were then subjected to cyclic voltammetry using a three-electrode system of a glassy carbon working electrode, a lithium counter electrode, and a Li/Li$^+$ reference electrode, at different scan rates. As shown in FIG. 6, a single redox couple was observed at a potential of about 4.47 V vs. Li/LP, with excellent reversibility.

Illustrative Claims

Para. A. An electrochemical device comprising a compound represented by Formula I:

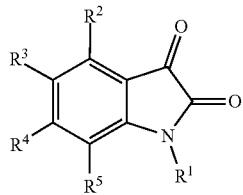

(I)

wherein:
$R^1$, $R^2$, $R^3$, $R^4$, and $R^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of $R^1$, $R^2$, $R^3$, $R^4$, and $R^5$ is a linker to a polymer backbone, where the linker is absent, a carbonyl, a alkyl ester group, aryl-E, E-aryl, alkylene, or -alkyl-O-alkyl-;
E is an alkylene or alkyl-O-alkyl;
at least one of $R^1$, $R^2$, $R^3$, $R^4$, and $R^5$ is other than H;
when $R^1$ is H, $R^3$ is other than methyl.

Para. B. The electrochemical device of Para. A, wherein $R^1$, $R^2$, $R^3$, $R^4$, and $R^5$ are each independently H, substituted or unsubstituted $C_1$-$C_{10}$ alkyl, substituted or unsubstituted $C_1$-$C_{10}$ alkoxy, substituted or unsubstituted $C_1$-$C_{10}$ haloalkyl, or polyether.

Para. C. The electrochemical device of Para. A or B, wherein $R^1$, $R^2$, $R^3$, $R^4$, and $R^5$ are each independently H, methyl, ethyl, n-propyl, i-propyl, n-butyl, sec-butyl, tert-butyl, or polyether.

Para. D. The electrochemical device of any of Paras. A-C, wherein $R^1$, $R^3$, and $R^5$ are each independently $C_1$-$C_{10}$ alkyl, and $R^2$ and $R^4$ are H.

Para. E. The electrochemical device of any of Paras. A-C, wherein $R^1$, $R^3$, and $R^5$ are each independently methyl, ethyl, n-propyl, i-propyl, n-butyl, sec-butyl, or tert-butyl; and $R^2$ and $R^4$ are H.

Para. F. The electrochemical device of any of any one of Paras. A-E, wherein $R^1$, $R^3$, and $R^5$ are each independently methyl or ethyl; and $R^2$ and $R^4$ are H.

Para. G. The electrochemical device of any of any one of Paras. A-F, wherein $R^3$ is a substituted aryl group of Formula II:

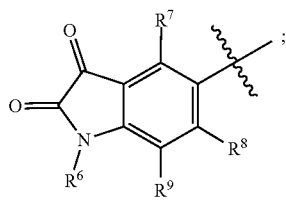

(II)

wherein $R^6$, $R^7$, $R^8$, and $R^9$ are each independently H, substituted or unsubstituted alkyl, substituted or unsubstituted alkoxy, substituted or unsubstituted haloalkyl, or substituted or unsubstituted polyether, or where any of $R^6$, $R^7$, $R^8$, and $R^9$ is a linker to a polymer backbone, where the linker is absent, an alkylenyl, an alkyl-O-alkyl, aryl-E, E-aryl, a carbonyl, or a alkyl ester, wherein E is an alkylene or alkyl-O-alkyl.

Para. H. The electrochemical device of any of any one of Paras. A-G, wherein $R^1$ or $R^3$ is a linker, L, to a polymer backbone, where the linker is absent, a carbonyl, alkylene, aryl-E, E-aryl, -alkyl-O-alkyl-, or a alkyl ester group, wherein E is an alkylenyl or alkyl-O-alkyl.

Para. I. The electrochemical device of any of any one of Paras. A-H. The electrochemical device of Claim 8, wherein the compound is of Formula III, IIIa, or IV:

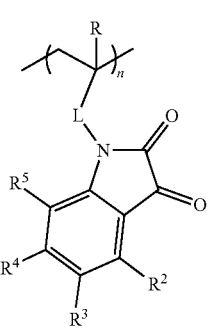

(III)

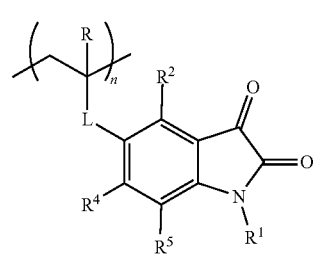

(IV)

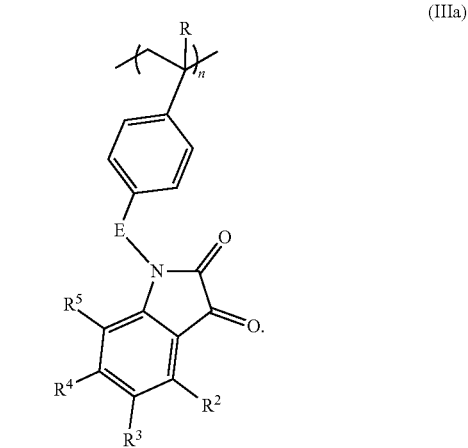

(IIIa)

wherein R is H or alkyl, and n indicates that this is part of a repeat unit in a polymer backbone.

Para. J. The electrochemical device of Para. I, wherein L is absent, —$CH_2$—, -alkyl-O-alkyl, —C(O)—, or —$CH_2CH_2OC(O)$—; and E is —$CH_2$— or alkyl-O-alkyl.

Para. K. The electrochemical device of Para. J, wherein the compound is represented by Formula III, and L is —C(O)— or —$CH_2CH_2OC(O)$—.

Para. L. The electrochemical device of any of any one of Paras. A-K, wherein R is $CH_3$.

Para. M. The electrochemical device of Para. I, wherein the compound is represented by Formula IV, and L is absent.

Para. N. The electrochemical device of Para. M, wherein R is H.

Para. O. The electrochemical device of any of any one of Paras. A-N, wherein $R^3$ is an aryl group of Formulae, where each ～ is a link to a group of Formula I:

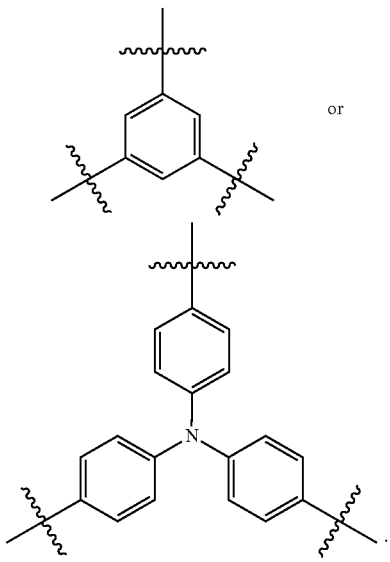

Para. P. The electrochemical device of any of any one of Paras. A-O, wherein $R^1$ is group of Formula Ia:

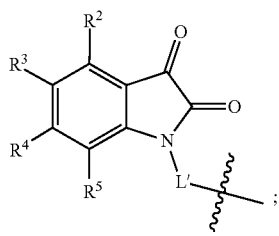

(Ia)

wherein and L' is absent or a linker group.

Para. Q. The electrochemical device of Para. P, wherein L' is a substituted or unsubstituted alkylene or alkyl-O-alkyl ether group.

Para. R. An electrochemical device comprising a compound represented by Formula V, VI, VI, or VII:

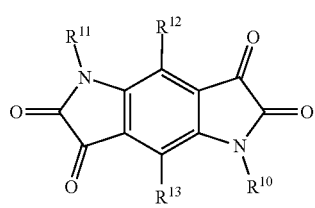

(V)

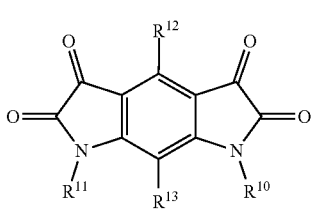

(VI)

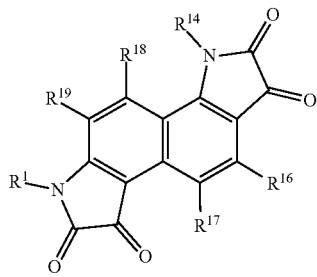

(VI)

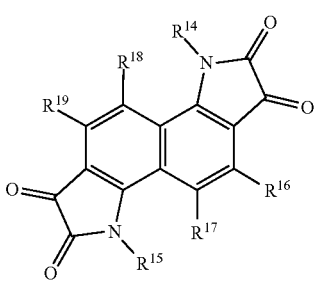

(VII)

wherein $R^{10}$, $R^{11}$, $R^{12}$, $R^{13}$, $R^{14}$, $R^{15}$, $R^{16}$, $R^{17}$, $R^{18}$, and $R^{19}$ are each independently H, substituted or unsubstituted alkyl, substituted or unsubstituted haloalkyl, substituted or unsubstituted alkoxy, or substituted or unsubstituted polyether; or where any of $R^1$, $R^2$, $R^3$, $R^4$, and $R^5$ is a linker to a polymer backbone, where the linker is absent, an alkylenyl, an alkyl-O-alkyl, aryl-E, E-aryl, a carbonyl, or a alkyl ester, wherein E is an alkylene or alkyl-O-alkyl.

Para. S. The electrochemical device of Para. R, wherein $R^{10}$, $R^{11}$, $R^{12}$, $R^{13}$, $R^{14}$, $R^{15}$, $R^{16}$, $R^{17}$, $R^{18}$, and $R^{19}$ are each independently H, substituted or unsubstituted $C_1$-$C_{10}$ alkyl, substituted or unsubstituted $C_1$-$C_{10}$ alkoxy, substituted or unsubstituted $C_1$-$C_{10}$ haloalkyl, or polyether.

Para. T. The electrochemical device of any of any one of Paras. R or S, wherein $R^{10}$, $R^{11}$, $R^{12}$, $R^{13}$, $R^{14}$, $R^{15}$, $R^{16}$, $R^{17}$, $R^{18}$, and $R^{19}$ are each independently H, methyl, ethyl, n-propyl, i-propyl, n-butyl, sec-butyl, tert-butyl, or polyether.

Para. U. The electrochemical device of any of any one of Paras. R-T, wherein $R^{10}$, $R^{11}$, $R^{14}$, or $R^{15}$ is a linker, L, to a polymer backbone, wherein L is absent, a carbonyl, a alkyl ester group, alkylene, or -alkyl-O-alkyl-.

Para. V. The electrochemical device of any of any one of Paras. A-U, which is a redox flow battery or lithium ion battery.

Para. W. An electrochemical device comprising: a cathode; an anode; a separator disposed between the cathode and the anode; and an electrolyte comprising: a non-aqueous solvent; a salt; and an isatin derivative that is other than isatin and 5-methylisatin; wherein the electrochemical device is a lithium ion battery or a sodium ion battery.

Para. X. The electrochemical device of Para. W, wherein the isatin derivative is a compound represented by Formula I:

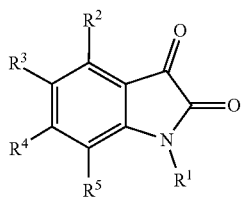

wherein
$R^1$, $R^2$, $R^3$, $R^4$, and $R^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of $R^1$, $R^2$, $R^3$, $R^4$, and $R^5$ is a linker to a polymer backbone, where the linker is absent, a carbonyl, aryl-E, E-aryl, a alkyl ester group, alkylene, or -alkyl-O-alkyl-;
E is an alkylene or alkyl-O-alkyl;
at least one of $R^1$, $R^2$, $R^3$, $R^4$, and $R^5$ is other than H;
when $R^1$ is H, $R^3$ is other than methyl.

Para. Y. The electrochemical device of Para. W or X, wherein the anode comprises a conductive carbon material.

Para. Z. The electrochemical device of any of any one of Paras. W-Y, wherein the cathode comprises a lithium transition metal oxide or a sodium transition metal oxide.

Para. AA. The electrochemical device of any of any one of Paras. W-Z, wherein the anode comprises a binder and current collector.

Para. AB. The electrochemical device of any of any one of Paras. W-AA, wherein the cathode comprises a binder and current collector.

Para. AC. An electrochemical device comprising: a catholyte reservoir containing a catholyte material dissolved in a first non-aqueous solvent; an anolyte reservoir containing an anolyte material dissolved in a second non-aqueous solvent; and a reaction chamber; wherein: the first and second non-aqueous solvents are the same or different; the catholyte material, the anolyte material, or both the catholyte material and the anolyte material is an isatin derivative compound; and the electrochemical device is a redox flow battery.

Para. AD. The electrochemical device of Para. AC, wherein the isatin derivative compound is other than isatin and 5-methylisatin.

Para. AE. The electrochemical device of Paras. AC or AD, wherein the isatin derivative is a compound represented by Formula I:

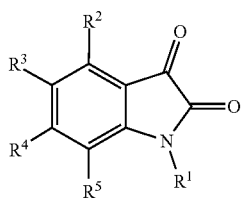

wherein:
$R^1$, $R^2$, $R^3$, $R^4$, and $R^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of $R^1$, $R^2$, $R^3$, $R^4$, and $R^5$ is a linker to a polymer backbone, where the linker is absent, an alkylenyl, an alkyl-O-alkyl, aryl-E, E-aryl, a carbonyl, or a alkyl ester, wherein E is an alkylene or alkyl-O-alkyl.

Para. AF. The electrochemical device of Para. AE, wherein at least one of $R^1$, $R^2$, $R^3$, $R^4$, and $R^5$ is other than H.

Para. AG. The electrochemical device of any of any one of Paras. AE-AF, wherein when $R^1$ is H, $R^3$ is other than methyl.

Para. AH. The electrochemical device of any of any one of Paras. AC-AG, wherein the catholyte and anolyte materials are both the isatin derivative.

Para. AI. The electrochemical device of any of any one of Paras. AC-AH, wherein the first and the second non-aqueous solvents are the same.

Para. AJ. A compound represented by Formula I:

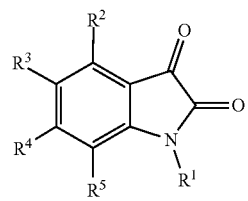

wherein:
$R^1$, $R^2$, $R^3$, $R^4$, and $R^5$ are each independently H, substituted or unsubstituted alkyl, substituted or unsubstituted haloalkyl, substituted or unsubstituted alkoxy, substituted or unsubstituted aryl, or substituted or unsubstituted polyether; or where any of $R^1$, $R^2$, $R^3$, $R^4$, and $R^5$ is a linker to a polymer backbone, where the linker is absent, an alkylenyl, an alkyl-O-alkyl, aryl-E, E-aryl, a carbonyl, or a alkyl ester, wherein E is an alkylene or alkyl-O-alkyl;
at least one of $R^1$, $R^2$, $R^3$, $R^4$, and $R^5$ is other than H;
when $R^1$ is H, $R^3$ is other than methyl; and
where $R^1$ is methyl, $R^3$ and $R^5$ are not both methyl.

Para. AK. The compound of Para. AJ, wherein $R^3$ is an aryl group of Formulae, where each so ⌇⌇⌇ is a link to a group of Formula I

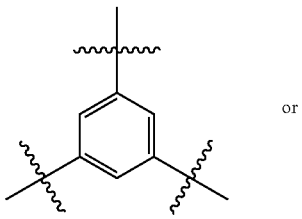

or

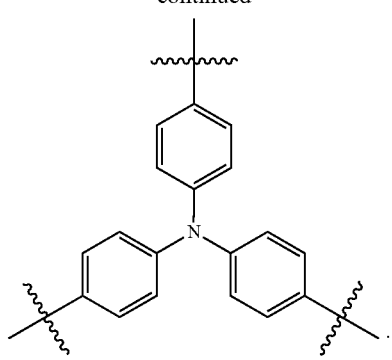
Para. AL. The compound of Para. AJ which is:
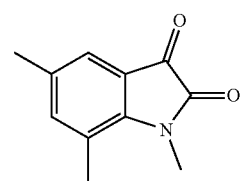
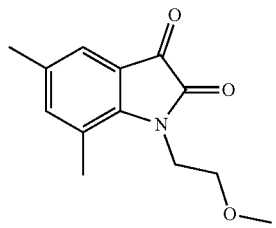
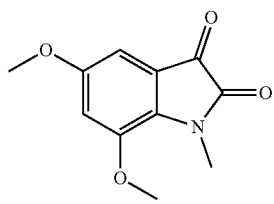
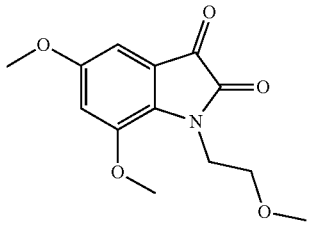
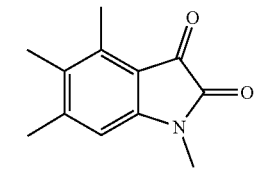
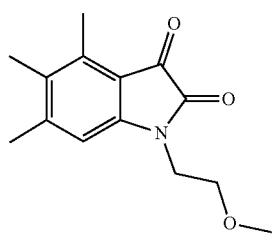
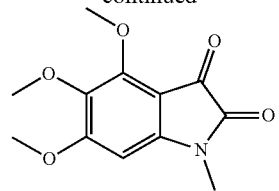
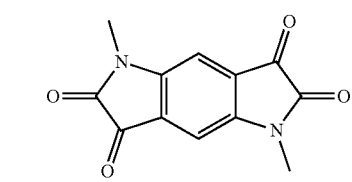
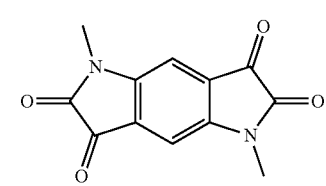
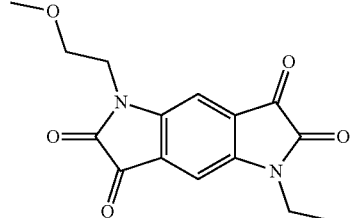
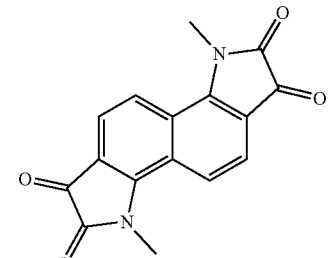
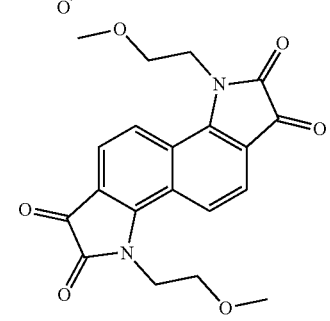

-continued

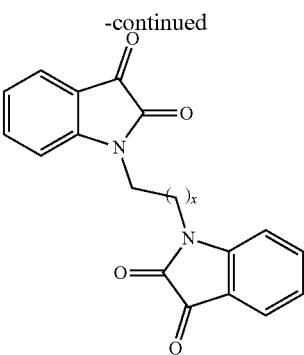

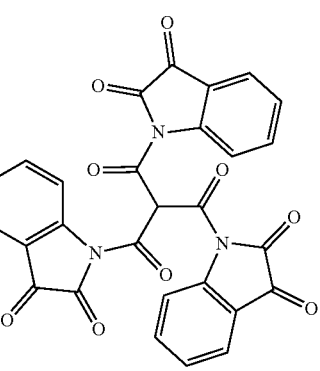

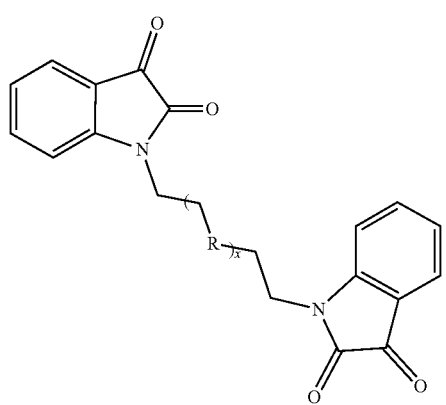

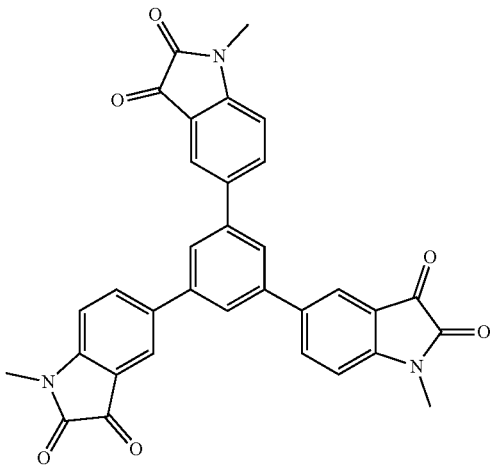

-continued

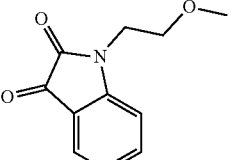

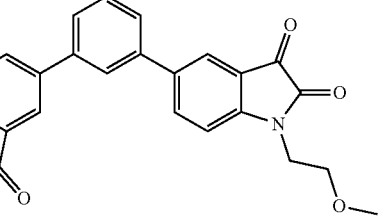

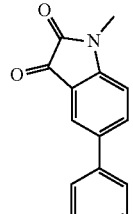

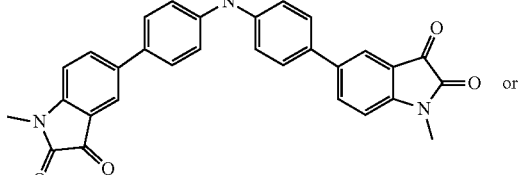

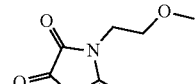

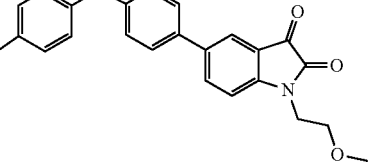

wherein x is 0 to 25 and R is ethylene oxide, O, S, N-alkyl, or C=O.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can of course vary. It is also to be understood that the terminology used herein is for describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An electrochemical device comprising a cathode, an anode, and an electrolyte comprising a compound represented by Formula I:

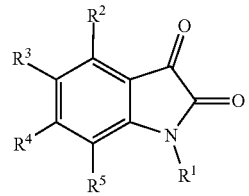

wherein:
$R^1$, $R^2$, $R^3$, $R^4$, and $R^5$ are each independently H, alkyl, haloalkyl, alkoxy, aryl, or polyether; or where any of $R^1$, $R^2$, $R^3$, $R^4$, and $R^5$ is a linker to a polymer backbone, where the linker is absent, a carbonyl, an alkyl ester group, aryl-E, E-aryl, alkylene, or -alkyl-O-alkyl-;
E is an alkylene or alkyl-O-alkyl;
at least one of $R^1$, $R^2$, $R^3$, $R^4$, and $R^5$ is other than H;
when $R^1$ is H, $R^3$ is other than methyl.

2. The electrochemical device of claim 1 which is a redox flow battery or lithium ion battery.

3. The electrochemical device of claim 1, wherein $R^1$, $R^2$, $R^3$, $R^4$, and $R^5$ are each independently H, $C_1$-$C_{10}$ alkyl, $C_1$-$C_{10}$ alkoxy, $C_1$-$C_{10}$ haloalkyl, or polyether.

4. The electrochemical device of claim 1, wherein $R^1$, $R^2$, $R^3$, $R^4$, and $R^5$ are each independently H, methyl, ethyl, n-propyl, i-propyl, n-butyl, sec-butyl, tert-butyl, or polyether.

5. The electrochemical device of claim 1, wherein $R^1$, $R^3$, and $R^5$ are each independently $C_1$-$C_{10}$ alkyl, and $R^2$ and $R^4$ are H.

6. The electrochemical device of claim 1, wherein $R^1$, $R^3$, and $R^5$ are each independently methyl, ethyl, n-propyl, i-propyl, n-butyl, sec-butyl, or tert-butyl; and $R^2$ and $R^4$ are H.

7. The electrochemical device of claim 1, wherein $R^1$, $R^3$, and $R^5$ are each independently methyl or ethyl; and $R^2$ and $R^4$ are H.

8. The electrochemical device of claim 1, wherein $R^3$ is an aryl group of Formulae, where each ⌇⌇⌇ is a link to a group of Formula I:

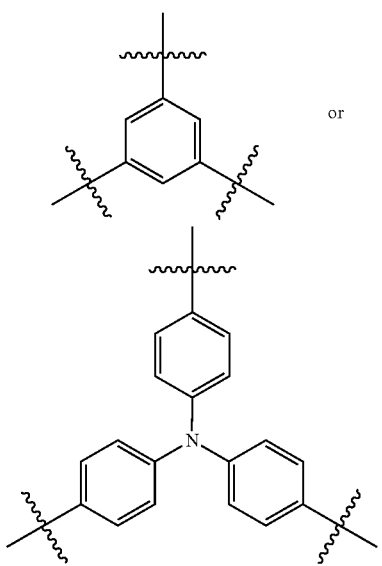

9. The electrochemical device of claim 1, wherein $R^3$ is an aryl group of Formula II:

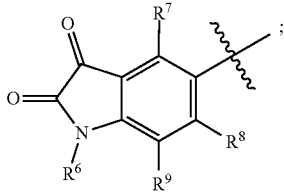

(II)

wherein $R^6$, $R^7$, $R^8$, and $R^9$ are each independently H, alkyl, alkoxy, haloalkyl, or polyether, or where any of $R^6$, $R^7$, $R^8$, and $R^9$ is a linker to a polymer backbone, where the linker is absent, an alkylenyl, an alkyl-O-alkyl, aryl-E, E-aryl, a carbonyl, or a alkyl ester, wherein E is an alkylene or alkyl-O-alkyl.

10. The electrochemical device of claim 1, wherein $R^1$ or $R^3$ is a linker, L, to a polymer backbone, where the linker is absent, a carbonyl, alkylene, aryl-E, E-aryl,-alkyl-O-alkyl-, or a alkyl ester group, wherein E is an alkylenyl or alkyl-O-alkyl.

11. The electrochemical device of claim 10, wherein the compound is of Formula III, IIIa, or IV:

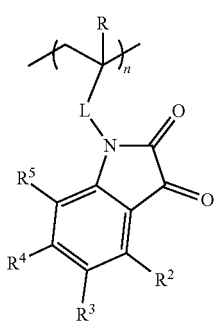

(III)

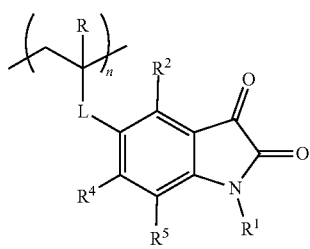

(IV)

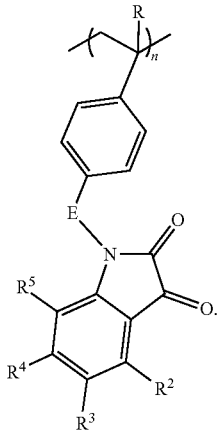

(IIIa)

wherein R is H or alkyl, and n indicates that this is part of a repeat unit in a polymer backbone.

12. The electrochemical device of claim 11, wherein L is absent, —$CH_2$—, -alkyl-O-alkyl, —C(O)—, or —$CH_2CH_2OC(O)$—; and E is —$CH_2$—or alkyl-O-alkyl.

13. An electrochemical device comprising:
a catholyte reservoir containing a catholyte material dissolved in a first non-aqueous solvent;
an anolyte reservoir containing an anolyte material dissolved in a second non-aqueous solvent; and
a reaction chamber;
wherein:
the first and second non-aqueous solvents are the same or different;
the catholyte material, the anolyte material, or both the catholyte material and the anolyte material is an isatin derivative compound;
the electrochemical device is a redox flow battery; and
the isatin derivative compound is represented by Formula I:

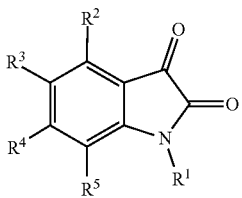

(I)

$R^1$, $R^2$, $R^3$, $R^4$, and $R^5$ are each independently H, alkyl, haloalkyl, alkoxy, aryl, or polyether; or where any of $R^1$, $R^2$, $R^3$, $R^4$, and $R^5$ is a linker to a polymer backbone, where the linker is absent, a carbonyl, aryl-E, E-aryl, an alkyl ester group, alkylene, or -alkyl-O-alkyl-; and
E is an alkylene or alkyl-O-alkyl;
wherein at least one of $R^1$, $R^2$, $R^3$, $R^4$, and $R^5$ is other than H; and
when $R^1$ is H, $R^3$ is other than methyl.

14. The electrochemical device of claim 13, wherein the catholyte and anolyte materials are both the isatin derivative.

15. The electrochemical device of claim 13, wherein the first and the second non-aqueous solvents are the same.

16. The electrochemical device of claim 13, wherein the isatin derivative is a compound represented by Formula I:

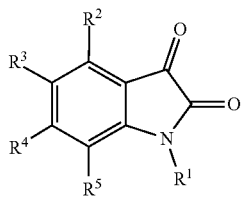

wherein:
R$^1$, R$^2$, R$^3$, R$^4$, and R$^5$ are each independently H, alkyl, haloalkyl, alkoxy, aryl, or polyether; or where any of R$^1$, R$^2$, R$^3$, R$^4$, and R$^5$ is a linker to a polymer backbone, where the linker is absent, an alkylenyl, an alkyl-O-alkyl, aryl-E, E-aryl, or an alkyl ester group, a alkyl ester, wherein E is an alkylene or alkyl-O-alkyl.

17. An electrochemical device comprising:
a cathode;
an anode;
a separator disposed between the cathode and the anode; and
an electrolyte comprising:
 a non-aqueous solvent;
 a salt; and
 an isatin derivative that is other than isatin and 5-methylisatin;

wherein:
the electrochemical device is a lithium ion battery or a sodium ion battery; and
the isatin derivative is a compound represented by Formula I:

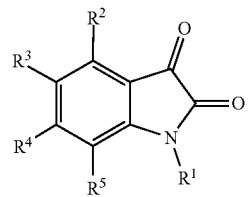

R$^1$, R$^2$, R$^3$, R$^4$, and R$^5$ are each independently H, alkyl, haloalkyl, alkoxy, aryl, or polyether; or where any of R$^1$, R$^2$, R$^3$, R$^4$, and R$^5$ is a linker to a polymer backbone, where the linker is absent, a carbonyl, aryl-E, E-aryl, an alkyl ester group, alkylene, or -alkyl-O-alkyl-; and
E is an alkylene or alkyl-O-alkyl;
wherein at least one of R$^1$, R$^2$, R$^3$, R$^4$, and R$^5$ is other than H; and
when R$^1$ is H, R$^3$ is other than methyl.

* * * * *